United States Patent
Gallagher et al.

(10) Patent No.: US 11,376,660 B2
(45) Date of Patent: Jul. 5, 2022

(54) PROCESSES FOR ADDITIVELY MANUFACTURING ORTHOPEDIC IMPLANTS

(71) Applicant: Titan Spine, Inc., Mequon, WI (US)

(72) Inventors: Michelle B. Gallagher, Mequon, WI (US); Jennifer M. Schneider, Mequon, WI (US); Mark E. Berg, Mequon, WI (US)

(73) Assignee: TITAN SPINE, INC., Mequon, WI (US)

(*) Notice: Subject to any disclaimer, the term of this patent is extended or adjusted under 35 U.S.C. 154(b) by 71 days.

(21) Appl. No.: 15/777,435

(22) PCT Filed: Nov. 21, 2016

(86) PCT No.: PCT/US2016/063064
§ 371 (c)(1),
(2) Date: May 18, 2018

(87) PCT Pub. No.: WO2017/087944
PCT Pub. Date: May 26, 2017

(65) Prior Publication Data
US 2018/0326493 A1     Nov. 15, 2018

Related U.S. Application Data
(60) Provisional application No. 62/258,251, filed on Nov. 20, 2015.

(51) Int. Cl.
B22F 3/24     (2006.01)
B22F 3/105    (2006.01)
(Continued)

(52) U.S. Cl.
CPC ............ *B22F 3/24* (2013.01); *A61F 2/30771* (2013.01); *A61F 2/447* (2013.01); *A61F 2/4455* (2013.01);
(Continued)

(58) Field of Classification Search
CPC ...... B22F 3/24; B22F 2998/10; B22F 3/1055; B22F 2301/205; B22F 3/15;
(Continued)

(56) References Cited

U.S. PATENT DOCUMENTS 3,891,456 A  6/1975 Hohman et al.
5,108,432 A  4/1992 Gustavson
(Continued)

FOREIGN PATENT DOCUMENTS

CA  2597249 A1  8/2006
CN  1392799 A   1/2003
(Continued)

OTHER PUBLICATIONS

Frye et al., The Effects of Hot Isostatic Pressing of Platinum Alloy Castings on Mechanical Properties and Microstructures, . Johnson Matthey Technol. Rev., 2015, 59, (3), 207-217, Jul. 1, 2015. (Year: 2015).*
(Continued)

*Primary Examiner* — Rebecca Janssen
(74) *Attorney, Agent, or Firm* — Womble Bond Dickinson (US) LLP

(57) ABSTRACT

Orthopedic implants produced by additive manufacture, followed by refinement of exterior and interior surfaces trough mechanical erosion, chemical erosion, or a combination of mechanical and chemical erosion. Surface refinement removes debris, and also produces bone-growth enhancing micro-scale and nano-scale structures.

16 Claims, 11 Drawing Sheets

(51) Int. Cl.
  *B33Y 10/00* (2015.01)
  *C22C 1/04* (2006.01)
  *B22F 3/15* (2006.01)
  *A61L 27/06* (2006.01)
  *A61F 2/44* (2006.01)
  *B33Y 80/00* (2015.01)
  *A61F 2/30* (2006.01)
  *B22F 10/20* (2021.01)

(52) U.S. Cl.
  CPC ............ *A61F 2/4465* (2013.01); *A61L 27/06* (2013.01); *B22F 10/20* (2021.01); *B33Y 10/00* (2014.12); *B33Y 80/00* (2014.12); *A61F 2/3094* (2013.01); *A61F 2002/3084* (2013.01); *A61F 2002/3097* (2013.01); *A61F 2002/30838* (2013.01); *A61F 2002/30968* (2013.01); *A61F 2002/30985* (2013.01); *A61L 2400/12* (2013.01); *A61L 2400/18* (2013.01); *A61L 2430/02* (2013.01); *B22F 3/15* (2013.01); *B22F 2003/241* (2013.01); *B22F 2003/247* (2013.01); *B22F 2301/205* (2013.01); *B22F 2998/10* (2013.01); *C22C 1/0458* (2013.01); *Y02P 10/25* (2015.11)

(58) Field of Classification Search
  CPC .............. B22F 2003/247; B22F 2003/241; B22F 5/10; B22F 2003/244; B33Y 80/00; B33Y 10/00; B33Y 40/00; A61L 2430/02; A61L 2400/12; A61L 2400/18; A61L 27/06; A61L 2400/18; A61L 27/04; A61F 2/447; A61F 2/4465; A61F 2/4455; A61F 2002/30985; A61F 2/30771; A61F 2002/30986; A61F 2002/3097; A61F 2002/30968; A61F 2002/3084; A61F 2002/30838; Y02P 10/295; C22C 1/0458; B24C 11/00; B24C 3/325; B24C 1/00; B24C 3/32
  See application file for complete search history.

(56) References Cited

U.S. PATENT DOCUMENTS

| | | | |
|---|---|---|---|
| 5,201,766 | A | 4/1993 | Georgette |
| 5,456,723 | A * | 10/1995 | Steinemann ........ A61F 2/30767 606/76 |
| 5,603,338 | A | 2/1997 | Beaty |
| 5,705,082 | A | 1/1998 | Hinson |
| 6,911,249 | B2 | 6/2005 | Wagner et al. |
| 8,277,577 | B2 | 10/2012 | Garcia Saban et al. |
| 8,814,939 | B2 | 8/2014 | Ullrich, Jr. et al. |
| 8,843,229 | B2 | 9/2014 | Vanasse et al. |
| 9,125,756 | B2 | 9/2015 | Ullrich, Jr. et al. |
| 9,149,989 | B2 | 10/2015 | Uckelmann |
| 9,848,995 | B2 | 12/2017 | Ullrich, Jr. et al. |
| 2004/0167633 | A1 | 8/2004 | Wen et al. |
| 2004/0265780 | A1 | 12/2004 | Robb et al. |
| 2006/0241760 | A1 | 10/2006 | Randall et al. |
| 2008/0261178 | A1 | 10/2008 | Homann et al. |
| 2010/0114303 | A1* | 5/2010 | Su ................. A61F 2/0077 623/1.46 |
| 2010/0218854 | A1 | 9/2010 | Garcia Saban et al. |
| 2011/0014081 | A1* | 1/2011 | Jones ................ A61F 2/2803 419/2 |
| 2011/0151026 | A1 | 6/2011 | Hansson et al. |
| 2011/0282454 | A1 | 11/2011 | Ullrich et al. |
| 2012/0303127 | A1 | 11/2012 | Ullrich et al. |
| 2012/0312778 | A1 | 12/2012 | Ullrich et al. |
| 2012/0316650 | A1 | 12/2012 | Ullrich, Jr. et al. |
| 2013/0056912 | A1 | 3/2013 | O'Neill et al. |
| 2013/0204384 | A1 | 8/2013 | Hensley et al. |
| 2013/0302509 | A1 | 11/2013 | McEntire et al. |
| 2013/0306591 | A1 | 11/2013 | Ullrich et al. |
| 2013/0310938 | A1 | 11/2013 | Soumac et al. |
| 2014/0025181 | A1 | 1/2014 | Vanasse et al. |
| 2014/0034368 | A1 | 2/2014 | Klamminger et al. |
| 2014/0048981 | A1 | 2/2014 | Crump et al. |
| 2014/0172111 | A1 | 6/2014 | Lang et al. |
| 2014/0195001 | A1 | 7/2014 | Grohowski, Jr. |
| 2014/0195005 | A1 | 7/2014 | McKay |
| 2014/0343687 | A1 | 11/2014 | Jennissen |
| 2015/0033543 | A1 | 2/2015 | Markwardt |
| 2015/0045903 | A1 | 2/2015 | Neal |
| 2015/0093719 | A1 | 4/2015 | Beeby |
| 2015/0320466 | A1 | 11/2015 | Kennedy et al. |
| 2015/0335434 | A1 | 11/2015 | Patterson et al. |
| 2017/0071744 | A1 | 3/2017 | Bali et al. |
| 2017/0173225 | A1 | 6/2017 | Troxel |
| 2017/0182222 | A1 | 6/2017 | Paddock et al. |
| 2017/0290666 | A1 | 10/2017 | Behzadi |
| 2018/0326493 | A1 | 11/2018 | Gallagher et al. |
| 2018/0333782 | A1* | 11/2018 | Gallagher .............. B33Y 10/00 |
| 2019/0142574 | A1* | 5/2019 | Quiros ................ B29C 33/3842 623/8 |
| 2019/0231535 | A1* | 8/2019 | Gallagher .............. A61B 17/58 |

FOREIGN PATENT DOCUMENTS

| | | |
|---|---|---|
| CN | 1638820 A | 7/2005 |
| CN | 101340934 A | 1/2009 |
| CN | 101634025 A | 1/2010 |
| CN | 101720209 A | 6/2010 |
| CN | 101848683 A | 9/2010 |
| CN | 102300518 A | 12/2011 |
| CN | 101686862 B | 8/2014 |
| EP | 1947217 B1 | 5/2012 |
| JP | H0130757 A | 5/1998 |
| JP | 2001000452 A | 6/2002 |
| JP | 2003521973 A | 7/2003 |
| JP | 2008-536535 | 9/2008 |
| JP | 2009526614 A | 7/2009 |
| JP | 2009189817 A | 8/2009 |
| JP | 2011092736 A | 5/2011 |
| JP | 2011194099 A | 10/2011 |
| JP | 2015512762 A | 4/2015 |
| WO | WO 2007045471 | 4/2007 |
| WO | 2014018325 | 1/2014 |
| WO | 2015157703 | 10/2015 |
| WO | WO 2015157703 | 10/2015 |
| WO | WO2017053480 A1 | 3/2017 |
| WO | WO2017087927 A1 | 5/2017 |
| WO | WO2017177046 A1 | 10/2017 |

OTHER PUBLICATIONS

Koch, Carl C.. (2007). Nanostructured Materials—Processing, Properties, and Applications (2nd Edition)—5.3.4.1 Hot Pressing. (pp. 210-211). William Andrew Publishing (Year: 2007).*
Hot Isostatic Pressing (HIP), Isostatic Pressing Association, http://ipa-web.org/about-ip/hip.html, Oct. 16, 2016. (Year: 2016).*
Dong Cong et al., "Research on the surface morphology and biocompatibility of laser rapid forming titanium implants", Chinese Journal of Oral Implantology, 2013, vol. 18, No. 4, pp. 215-218. (Year: 2013).*
International Search Report issued in related application PCT/US2016/063034 dated Mar. 2, 2017.
Amin Yavari Saber et al, "Bone Regeneration Performance of Surface-Treated Porous Titanium", Biomaterials, May 6, 2014, XP029030462, vol. 35(24): 6172-6181.
Baek, W-Y, et al. "Positive Regulation of Adult Bone Formation by Osteoblast-Specific Transcription Factor Osterix", Journal of Bone Mineral Research, Dec. 29, 2008, vol. 24, No. 6, pp. 1055-1065.
Zhang, C., "Transcriptional regulation of bone formation by the osteoblast-specific transcription factor Osx", Journal of Orthopaedic Surgery and Research, Jun. 15, 2010, vol. 5, No. 37.
Tu et al., "Osterix Overexpression in Mesenchymal Stem cells Stimulates Healing of Critical-Sized Defects in Murine Calvarial Bone", Tissue Engineering, Oct. 2007, vol. 13, No. 10, pp. 2431-2440.

(56) References Cited

OTHER PUBLICATIONS

Leung, K.S. et al. "Plasma Bone-Specific Alkaline Phosphatase as an Indicator of Osteoblastic Activity", Journal of Bone & Joint Surgery, Jul. 14, 1992, vol. 75, No. 2, pp. 288-292.
Herrmann et al., "Different Kinetics of Bone Markers in Normal and Delayed Fracture Healing of Long Bones", Clinical Chemistry, Dec. 2002, vol. 48, Issue 12, pp. 2263-2266.
Borden M, et al., "The sintered microsphere matrix for bone tissue engineering: In vitro osteoconductivity studies", Journal of Biomedical Materials Research, Dec. 2001, vol. 61, No. 3, pp. 421-429.
Borden M, et al., "Tissue engineered microsphere-based matrices for bone repair: design and evaluation", Biomaterials, Apr. 3, 2001, vol. 23, pp. 551-559.
Borden M, et al., "Tissue-engineered bone formation in vivo using a novel sintered polymeric microsphere matrix", Journal of Bone and Joint Surgery, Jan. 15, 2004, vol. 86, pp. 1200-1208.
Datta et al., "Effect of bone extracellular matrix synthesized in vitro on the osteoblastic differentiation of marrow stromal cells", Biomaterials, Jul. 21, 2004, vol. 26, No. 9, pp. 971-977.
Bancroft et al., "Fluid flow increases mineralized matrix deposition in 3D perfusion culture of marrow stromal osteoblasts in a dose-dependent manner", Proceedings of the National Academy of the Sciences of the U.S.A., Oct. 1, 2002, vol. 99, No. 20, pp. 12600-12605.
Sikavitsas et al., "Influence of the in vitro culture period on the in vivo performance of cell/titanium bone tissue-engineered constructs using a rat cranial critical size defect model", Journal of Biomedical Materials Research, Mar. 31, 2003, vol. 67, No. 3, pp. 944-951.
First Office Action, dated Dec. 3, 2019, for Chinese Patent Application No. 201680079137.8.
Tammas-Williams Samuel et al: "The Effectiveness of Hot Isostatic Pressing for Closing Porosity in Titanium Parts Manufactured by Selective Electron Beam Melting", Metallurgical and Materials Transactions A: Physical Metallurgy& Materials Science, ASMInternational, Materials Park, OH, US, Mar. 16, 2016, vol. 47, No. 5, pp. 1939-1946.
Matteson et al., "Assessing the hierarchical structure of titanium implant surfaces", May 7, 2015, Journal of Biomedical Materials Research B: Applied Biomaterials, vol. 00b, Issue 00.
Westfall, Kurtosis as Peakedness, 1905-2014. R. I. P., Am Stat. 2014 ; 68(3): 191-195 (Year: 2014).
Anonymous: "Hot isostatic pressing—Wikipedia", Mar. 19, 2019 (Mar. 19, 2019), XP55571109; Retrieved from the internet: URL:https://en.wikipedia.org/wiki/Hot_isostatic-pressing [retrieved on Mar. 19, 2019].
Astra Tech Dental "Nanolevel topographic modifications on the OsseoSpeed surface", http://shop.dentsplyimplants.us, Mar. 8, 2001.
Eurocoating, "Additive Manufacturing: long-term specialist expertise in manufacturing implantable devices", Additive Manufacturing, 2008, Eurocoating spa, Trento Italy, www.eurocoating.it.
E-Manufacturing Solutions, "Additive Manufacturing in the Medical Field", Medical, Mar. 2013, e-Manufacturing Solutions, Krailing/Munich Germany, www.eos.info.
Guo, et al., "The effect of hydrofluoric acid treatment of TiO2 grit blasted titanium implants on adherent osteoblast gene expression in vitro and in vivo", Biomaterials 28, Sep. 14, 2007, 5418-5425.
He, et al., "Mechanical and Histomorphometric Evaluations of Rough Titanium Implants Treated with Hydrofluoric Acid, Nitric Acid Solution in Rabbit Tibia", Int J. Oral Maxillofac., Implants, Nov. 1, 2011; 26; 115-122.
ipmd.net, "Powder Metallurgy Review", 2012, ipmd.net, pp. 1-32, www.ipmd.net.
Isa, et al., "Effects of Fluoride-Modified Titanium Surfaces on Osteoblast Proliferation and Gene Expression", Int. J. Oral Maxillofac, Implants, 2006, 21 :203-211.
Lamolle et al., "The effect of hydrofluoric acid treatment of titanium surface on nanostructural and chemical changes and the growth of MC3T3-E1 cells", Biomaterials 30 (Nov. 20, 2008) 736-742.
Layerwise, "Medical Applications", Layerwise, 2012, Belgium, www.layerwise.com, www.dentwise.eu.
Meirelles, et al., "The Effect of Chemical and Nanotopographical Modifications on the Early Stages of Osseointegration", Int. J. Oral Maxillofac, Implants 2008, 23, 641-647.
Variola et al., "Nanoscale surface modifications of medically relevant metals: state-of-the-art and perspectives", Nanoscale, 2011, 3, 335-353.
Wennerberg, A., et al., "Effects of titanium surface topography on bone integration: a systematic review", Clin. Oral. lmpl. Res. 20, (Suppl. 4), 2009, pp. 172-184.
Wennerberg, et al., "Spontaneously formed nanostructures on titanium surfaces", Clin Oral lmpl Res, 2012, 1-7.
Communication pursuant to Article 94(3) EPC dated May 12, 2020, from European Appln. No. 16810170.7.
M. Thone et al: "Influence of heat-treatment on selective laser melting products—e.g. Ti6A 14V", SFF Symposium, Aug. 22, 2012, pp. 492-498, Retrieved from the Internet: URL:https://sffsymposium.engr.utexas.edu/Manuscripts/2012/2012-38-Thoene.pdf.
Notification of Reasons for Rejection dated Oct. 2, 2020, for Japanese Patent Application No. 2018-545569.
Notice of Reasons for Rejection dated Jan. 4, 2021, from Japanese Appln. No. 2018-545569.
Notifice of the Second Office Action dated Dec. 16, 2020, for Chinese Patent Application No. 201680079137.8.
Dong Cong et al., "Research on the surface morphology and biocompatibility of laser rapid forming titanium implants", Chinese Journal of Oral Implantology, 2013, vol. 18, No. 4, pp. 215-218.
Fernandez-Zelaia et al. "Crystallographic texture control in electron beam additive manufacturing via conductive manipulation" Materials and Design, vol. 195, Jul. 31, 2020, pp. 1-10.
Thijs et al. "A study of the microstructural evolution during selective laser melting of Ti-6Al4V" Acta Materialia, vol. 58, Issue 9, Mar. 16, 2010, pp. 3303-3312.
Yan, Fuyao, et al., "Grain Structure Control of Additively Manufactured Metallic Materials," Materials 2017, 10, 1260, Nov. 2, 2017, 11 pages.
Examination Report for Australian Application No. 2016355581 dated Sep. 1, 2021, 3 pages.
Decision on Rejection dated Jun. 28, 2021 for Chinese Patent Application No. 201680079137.8.
Notice of Reasons for Rejection dated Mar. 10, 2021, from Japanese Appln. No 2018-545569.
The National Institute for Occupational Safety and Health (NIOSH), "Preventing Silicosis and Deaths from Sandblasting," Center for Disease Control and Prevention, Aug. 1992, 13 pages.

* cited by examiner

PROCESSES FOR ADDITIVELY MANUFACTURING ORTHOPEDIC IMPLANTS

CROSS REFERENCE TO RELATED APPLICATIONS

This application claims priority to International Patent Application PCT/US2016/063064 filed on Nov. 21, 2016, which claims priority to U.S. Provisional Application No. 62/258,251, filed on Nov. 20, 2015, the contents of which are incorporated by reference herein, in their entirety and for all purposes.

FIELD OF THE INVENTION

The invention relates generally to the field of medical implant manufacture. In particular, the invention relates to a production process in which medical implants are built by an additive process, with the production process including, in any order, stress-relief or hot isostatic or hot uniaxial pressure, and/or eroding of external surfaces and, in some aspects, also eroding of internal surfaces of the implant.

BACKGROUND OF THE INVENTION

Various publications, including patents, published applications, technical articles and scholarly articles are cited throughout the specification. Each of these cited publications is incorporated by reference herein, in its entirety and for all purposes.

Orthopedic implants can be manufactured using conventional subtractive methods; milling, turning, drilling or sawing. They can also be produced using additive methods where materials in crystal or granular form are melted by energy sources and layered or applied while liquid to each other to form growing structures. Nevertheless, implants produced additively have not been realized to their full potential to promote bone integration and fusion. There remains a need in the art to extrapolate and add to the unique attributes afforded by the additive manufacture process.

SUMMARY OF THE INVENTION

The invention features methods for producing orthopedic implants, which implants have nano-scale structures that facilitate bone growth. The methods generally comprise additively building an orthopedic implant according to a desired shape. Following additively building the implant, the production process includes, in any order, stress-relieving the implant or treating the implant with hot isostatic pressure, or treating the implant with hot uniaxial pressure, and/or eroding one or more surfaces of the implant. Eroding may comprise mechanically eroding (e.g., blasting the surfaces with an organic or inorganic medium, which is preferably dissolvable, and may be particulate), chemically eroding (e.g., treating the surfaces with an acid or base), or a sequence of mechanical and chemical erosion. The orthopedic implants are preferably metallic, and not polymeric. The metal is preferably titanium or an alloy thereof. The titanium alloy may comprise an alloy of titanium, aluminum, and vanadium or may comprise nitinol.

The additive build may comprise successive layering and melting of powder, particles, granules, wires, fragments, or combinations thereof of the metal into the shape of the orthopedic implant, or successive layering of pre-melted metal. The additive build may comprise successive layering and sintering of powder, particles, granules, wires, fragments, or combinations thereof of the metal into the shape of the orthopedic implant. The additive build may comprise successive layering and alternating melting and sintering of powder, particles, granules, wires, fragments, or combinations thereof of the metal into the shape of the orthopedic implant. During additive building, a layer may be allowed to partially or fully solidify before the next layer is laid. The additive building preferably proceeds in a vertical build direction. In some aspects, the additive building proceeds in a horizontal build direction.

The mechanical eroding may comprise eroding the one or more surfaces with an organic or inorganic media. The media are preferably dissolvable in an aqueous medium, including an acidic aqueous medium or an alkaline aqueous media. The mechanical erosion preferably imparts micro-scale structures into the one or more surfaces. The micro-scale structures may comprise a maximum peak-to-valley height of from about 1 µm to about 200 µm. The micro-scale structures may comprise a skewness of from about −2 to about 2. The micro-scale structures may comprise a kurtosis of from about 1 to about 9. The micro-scale structures may comprise a maximum peak-to-valley height of from about 1 µm to about 200 µm and a skewness of from about −2 to about 2. The micro-scale structures may comprise a maximum peak-to-valley height of from about 1 µm to about 200 µm and a kurtosis of from about 1 to about 9. The micro-scale structures may comprise a maximum peak-to-valley height of from about 1 µm to about 200 µm, a skewness of from about −2 to about 2, and a kurtosis of from about 1 to about 9. In some aspects, mechanical eroding removes particulate debris from the one or more surfaces. The debris may comprise partially or fully unmelted or unsintered powder, particles, granules, wires, fragments, or combinations thereof of the metal. External surfaces may be mechanically eroded. Internal surfaces may be mechanically eroded. The eroded surfaces may contact bone or a bone graft material upon implantation of the implant within the body. The eroded surfaces may facilitate new bone growth such that the surfaces do not contact bone or a bone graft material immediately upon and following implantation, but contact bone a period of time following implantation when new bone grows on and out from such surfaces. In some aspects, mechanical erosion is employed without further chemical erosion.

The chemical erosion may comprise chemically eroding the one or more surfaces of the orthopedic implant, for example, with an acid or with a base. The implant may be immersed in an acid solution or a base solution in order to carry out the chemical eroding. Chemical eroding preferably imparts nano-scale structures into the one or more surfaces. The nano-scale structures may comprise a maximum peak to valley height of from about 0.001 µm to about 20 µm. Similar to mechanical erosion, the chemical erosion also can impart micro-scale structures into the one or more surfaces, including micro-scale structures comprising a maximum peak-to-valley height of from about 1 µm to about 200 µm, a skewness of from about −2 to about 2, and a kurtosis of from about 1 to about 9. Chemical eroding preferably also removes particulate debris from the one or more surfaces. The debris may comprise partially or fully unmelted or unsintered powder, particles, granules, wires, fragments, or combinations thereof of the metal. The debris may comprise the medium used during the mechanical eroding step, where components of the medium have embedded in the one or more surfaces. External surfaces may be chemically eroded. Internal surfaces may be chemically eroded. The eroded surfaces may contact bone or a bone graft material upon implantation of the implant within the body. The eroded surfaces may facilitate new bone growth such that the surfaces do not contact bone or a bone graft material immediately upon and following implantation, but contact bone a period of time following implantation when new bone grows on and out from such surfaces. In preferred aspects, chemical erosion follows mechanical erosion. In some alternative aspects, chemical erosion is employed without mechanical erosion.

The method may comprise a stress-relieving step. The method may comprise heating the implant and compressing the heated implant under hot isostatic pressure (HIP). The method may comprise heating the implant and compressing the heated implant under hot uniaxial pressing (HUP). In some aspects, the stress-relieving step, the HIP step, or the HUP step, if included, follow the additive building step and are before the mechanical erosion step, or before the chemical erosion step where only chemical erosion (no mechanical erosion) is used. In some aspects, the stress-relieving step, the HIP step, or the HUP step, if included, follow the chemical erosion step, or follow the mechanical erosion step where only mechanical erosion (no chemical erosion) is used.

In some aspects, the invention features methods for producing a metal orthopedic implant, comprising vertically additively building the orthopedic implant, then stress-relieving the orthopedic implant or heating the orthopedic implant and compressing the heated implant under hot isostatic pressure or under hot uniaxial pressure. In some alternative aspects, the method comprises horizontally additively building the orthopedic implant. Additively building the orthopedic implant comprises melting or sintering powder, particles, granules, wires, fragments, or combinations thereof of the metal into the shape of the orthopedic implant. Following the stress-relieving or heating and compressing steps, the methods may further comprise eroding one or more surfaces of the orthopedic implant. In some alternative embodiments, the stress-relieving or heating and compressing steps follow the eroding steps. The metal is preferably titanium or an alloy thereof. The titanium alloy may comprises an alloy of titanium, aluminum, and vanadium or may comprise nitinol.

The heating and/or stress-relieving steps may be carried out under a vacuum. The heating and/or stress-relieving steps may be carried out under atmospheric pressure and in an inert environment. In some aspects, the compressing substantially eliminates internal pores of the metal.

The mechanical eroding may comprise eroding the one or more surfaces with an organic or inorganic medium. The organic or inorganic media used for eroding are preferably dissolvable in an aqueous medium, including an acidic aqueous medium or an alkaline aqueous medium. The mechanical erosion preferably imparts micro-scale structures into the one or more surfaces. The micro-scale structures may comprise a maximum peak-to-valley height of from about 1 µm to about 200 µm, a skewness of from about −2 to about 2, and a kurtosis of from about 1 to about 9. In some aspects, mechanical eroding removes particulate debris from the one or more surfaces. The debris may comprise partially or fully unmelted or unsintered powder, particles, granules, wires, fragments, or combinations thereof of the metal. External surfaces may be mechanically eroded. Internal surfaces may be mechanically eroded. The eroded surfaces may contact bone or a bone graft material upon implantation of the implant within the body. The eroded surfaces may facilitate new bone growth such that the surfaces do not contact bone or a bone graft material immediately upon and following implantation, but contact bone a period of time following implantation when new bone grows on and out from such surfaces.

The chemical erosion may comprise chemically eroding the one or more surfaces of the orthopedic implant, for example, with an acid or with a base. The implant may be immersed in an acid solution or base solution in order to carry out the chemical eroding. Chemical eroding preferably imparts nano-scale structures into the one or more surfaces. The nano-scale structures may comprise a maximum peak to valley height of from about 0.001 µm to about 20 µm. The chemical erosion also can impart micro-scale structures into the one or more surfaces, including micro-scale structures comprising a maximum peak-to-valley height of from about 1 µm to about 200 µm, a skewness of from about −2 to about 2, and a kurtosis of from about 1 to about 9. Chemical eroding preferably also removes particulate debris from the one or more surfaces. The debris may comprise partially or fully unmelted or unsintered powder, particles, granules, wires, fragments, or combinations thereof of the metal. The debris may comprise the medium used during the mechanical eroding step, where such components of the medium have embedded in the one or more surfaces. External surfaces may be chemically eroded. Internal surfaces may be chemically eroded. The eroded surfaces may contact bone or a bone graft material upon implantation of the implant within the body. The eroded surfaces may facilitate new bone growth such that the surfaces do not contact bone or a bone graft material immediately upon and following implantation, but contact bone a period of time following implantation when new bone grows on and out from such surfaces. In preferred aspects, chemical erosion follows mechanical erosion. In some alternative aspects, chemical erosion is employed without mechanical erosion.

Orthopedic implants produced according to any method described or exemplified herein are further provided.

DETAILED DESCRIPTION OF THE INVENTION

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

A "patient" may be any animal, including mammals such as companion animals, laboratory animals, and non-human primates. Human beings are preferred.

Figure 1:
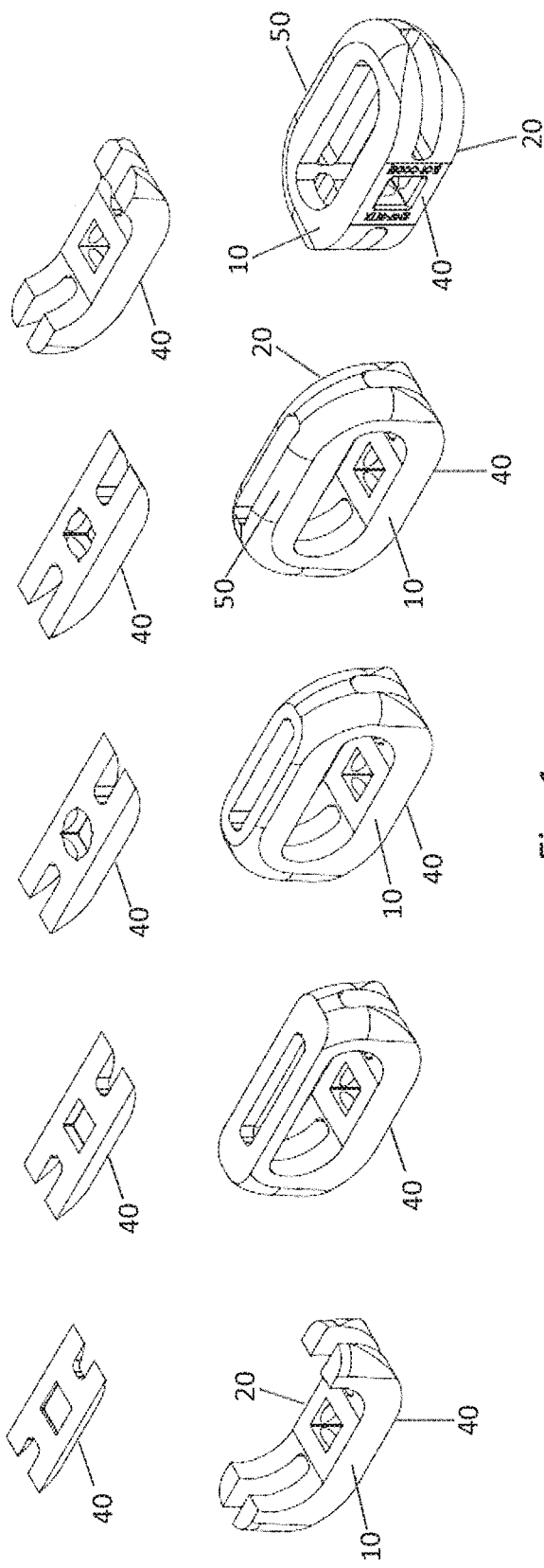
FIG. 1 shows an example of an additive manufacture process in which an implant is produced in layers from the anterior side (40) of the implant to the posterior side (50) of the implant. The top (10) and bottom (20) of the implant are bone-contacting surfaces.
Figure 2:
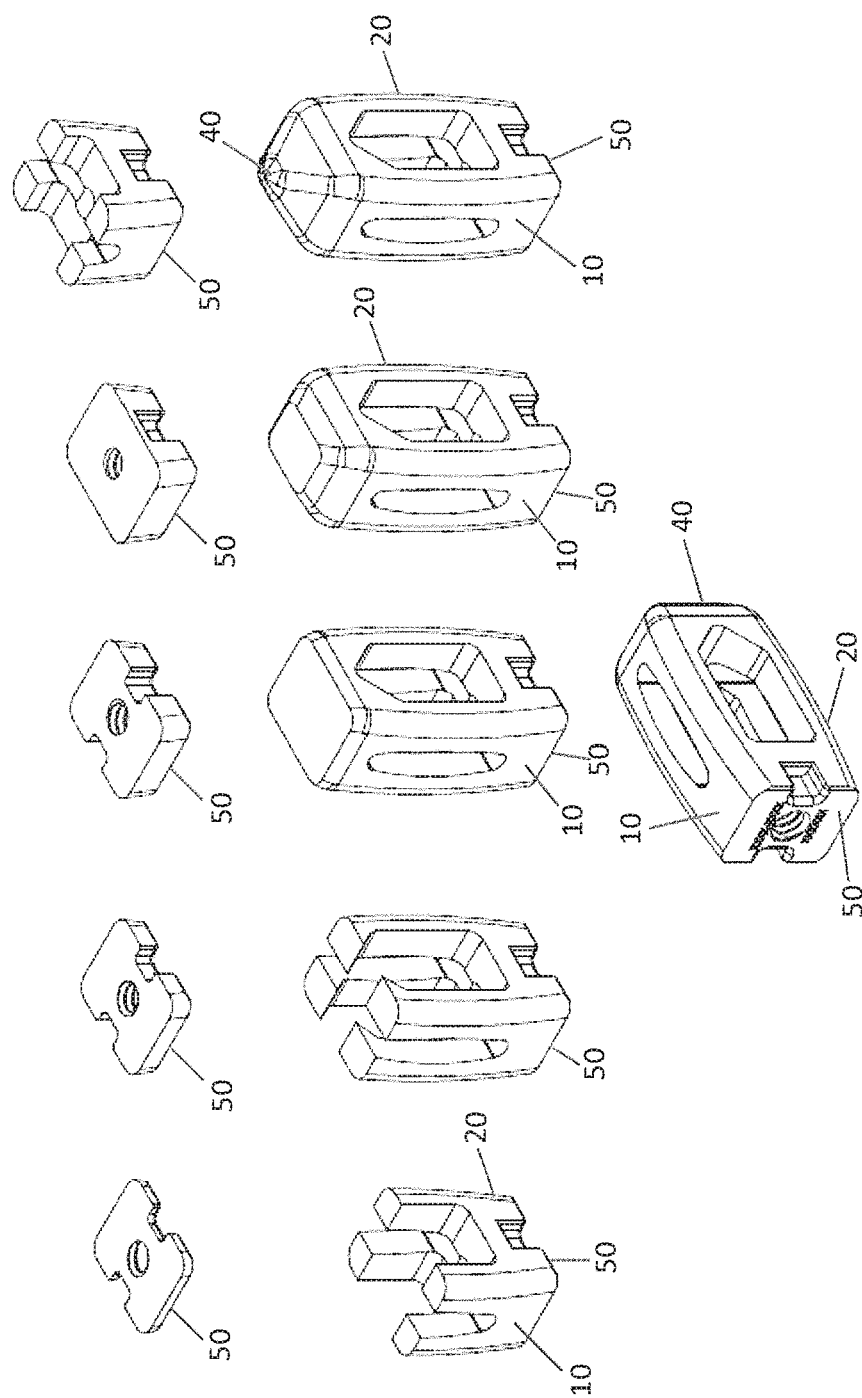
FIG. 2 shows an example of an additive manufacture process in which an implant is produced in layers from the posterior side (50) of the implant to the anterior side (40) of the implant. The top (10) and bottom (20) of the implant are bone-contacting surfaces.

"Vertically" additively building an orthopedic implant means that during the additive manufacture process, the build begins with a surface of the implant that does not contact bone such that the bone-contacting surfaces result from one or more of the edges of the additively-laid layers. By way of example, but not of limitation, if the top or bottom surfaces of an orthopedic implant are intended to contact bone but sides of the implant are not intended to contact bone, then the build begins with one of the sides of the implant, and the bone-contacting top and bottom arise as the layers are deposited. Vertical additive manufacture stands in contrast "horizontally" additively building an orthopedic implant. FIG. 1 and FIG. 2 show an additive process in which the implant is produced in an anterior to posterior (FIG. 1) or posterior to anterior (FIG. 2) direction, whereby the bone-contacting surfaces (10, 20) are the "sides" as the implant is additively manufactured, though the anterior (40) and posterior (50) surfaces are not bone-contacting surfaces.

Figure 3:
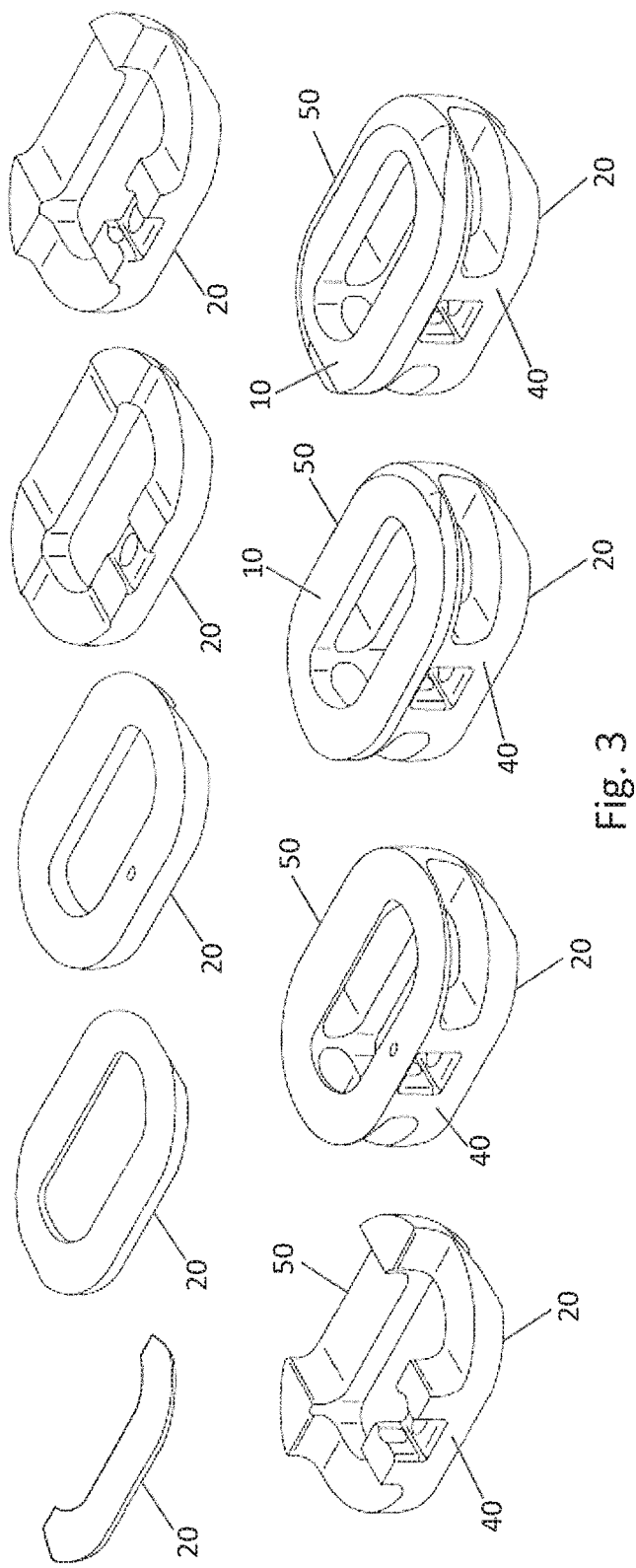
FIG. 3 shows an example of an additive manufacture process in which an implant is produced in layers from the bottom (20) of the implant to the top of the implant (10), which each are bone-contacting surfaces. The anterior (40) and posterior (50) sides are also indicated.

"Horizontally" additively building an orthopedic implant means that during the additive manufacture process, the build begins with a bone contacting surface. By way of example, but not of limitation, if the top or bottom surfaces of an orthopedic implant are intended to contact bone but sides of the implant are not intended to contact bone, then with horizontal additive manufacturing, the build begins with either of the bone-contacting top or bottom layers. FIG. 3 shows an additive process in which the implant is produced in a top to bottom direction, whereby the bone-contacting surfaces (10, 20) are the bottom as the additive manufacture begins, and are also the top when the additive manufacture concludes, and the anterior (40) and posterior (50) surfaces, which are not bone-contacting surfaces, are the "sides" as the implant is additively manufactured.

As used herein, "osteoinduction" and "osteoinducting" refers to the induction or initiation of osteogenesis, and includes the recruitment of immature mesenchymal stem cells to a processed (e.g., mechanically and/or chemically eroded) bone-contacting surface and/or to a processed (e.g., mechanically and/or chemically eroded) free surface of an orthopedic implant, followed by the phenotype progression and differentiation of these stem cells to a preosteoblast and the further phenotype progression and differentiation of a preosteoblast to an osteoblast.

"Osteogenesis" includes the formation and development of bone matrix.

It has been observed in accordance with the invention that additive building of implants, followed by erosion of certain external and internal surfaces of the implants produces implants with surfaces that enhance osteoinduction. It was further observed that the additive build direction can further influence this enhancement, with vertical additive building showing significant improvements over horizontal additive building. Implant surfaces produced additively, followed by subtractive processing (e.g., erosion) facilitate osteoinduction and, ultimately, support and facilitate integration of the implant with adjacent bone. Without intending to be limited to any particular theory or mechanism of action, it is believed that orthopedic implant surfaces produced in this way support greater mesenchymal stem cell differentiation and progression to a preosteoblast, and further differentiation and progression of a preosteoblast to an osteoblast. Such differentiation is characterized, for example, by greater production of growth factors associated with osteogenesis in vivo. Orthopedic implant surfaces produced by additive building followed by mechanical and/or chemical (e.g., acid) erosion are believed to support bone growth out from the surfaces, even in the absence of direct contact with bone or bone graft materials.

The combination of additive manufacture and erosion, in accordance with the inventive methods, produces macro-scale structural features, micro-scale structural features, and nano-scale structural features. It is believed that the macro-scale structural features facilitate and improve initial stability of the implant upon implantation, and that micro- and nano-scale structural features improve and facilitate the cellular and molecular response. For the most part, additive manufacturing produces a surface that, at the cellular level, does not induce a cellular and molecular response insofar as the structural features of the surface are too large in scale to be recognized by a cell sufficiently to induce the cell to activate, differentiate, or alter its phenotype. It is believed that this is due, in part, to the limitations in particle size and layer thickness. Erosion of the additively-produced surfaces, which creates the micro- and nano-scale structural features, is believed to establish a microstructure that can be recognized by cells (e.g., mesenchymal stem cells, preosteoblasts, etc.) sufficient to activate a bone growth response. It is believed that this microstructure is influenced by build orientation (e.g., horizontal versus vertical building).

In general, implant manufacture according to the invention comprises the basic steps of producing the implant body through an additive manufacturing process, and then refining one or more surfaces of the implant body to produce a bone growth-stimulating surface topography comprising micro-scale structural features and nano-scale structural features. In some aspects, this surface topography is irregular, including irregularities in the height, spacing, orientation, thickness, and other structural features between and among the micro-scale and/or nano-scale structures that make up the topography.

In some aspects, implant fabrication begins with engineering and designing the implant, including its geometry, dimensions, and structural features. The implant may comprise, for example, a top surface, a bottom surface, at least one posterior side surface, at least one anterior side surface, and at least one lateral side surface. The implant may comprise flat, round, regular, and/or irregular surfaces about these top, bottom, or side surfaces. The implant may comprise any suitable shape, which shape may depend, for example, on the intended implantation location. In highly preferred aspects, the implant is intended for integration with the surrounding bone. Implant engineering and design may be computer assisted.

The implant may comprise any implant that, when implanted, is in contact with at least one or is in between two or more bones, and which is intended to induce fusion or physical joining of the separate bones, or to facilitate rejoinder of broken bones. The implant may be used to replace, repair, brace, or supplement any bone in the body. The implant may comprise a long or short bone (or portion thereof) replacement, a skull or jaw bone replacement, an implant intended to induce fusion or physical joining of separate bones (e.g., finger joints, ankle joints, vertebrae, or spinal motion segment), an implant intended to fasten another implant to a bone (e.g., bone screws, pedicle screws, and fixation elements), an implant to facilitate rejoinder of broken bones, including bone screws, intramedullary nail, rods, and plates, etc., or any implant to replace, repair, brace, or supplement any bone in the body. In some aspects, the implant comprises an implant for replacing an intervertebral disc, or for replacing a spinal motion segment. The implant may comprise a joint implant, for example, an implant for the hip, knee, shoulder, elbow, ankle, wrist, jaw, etc.

It is preferred that implant fabrication comprises an additive manufacturing process. A form of 3-D printing may be part of the additive manufacturing process. The process comprises first additively building an orthopedic implant, e.g., the implant body having the desired basic shape, configuration, and structural orientation for the particular location within the body where the implant is to be implanted and for the particular corrective application intended for the implant, and then treating one or more surfaces of the implant, for example, with an erosion process. The erosion may comprise mechanical erosion, chemical erosion, or a combination of mechanical and chemical erosion. The implant surfaces treated with such erosion comprise a bone growth-enhancing bioactive surface topography comprising micro-scale structural features and nano-scale structural features.

The implants may be prepared from any suitable material, including a metal, a polymer, a ceramic, bone, or any combination or composite thereof. Metal implants may comprise an alloy. Preferred metals include titanium and titanium alloys such as nitinol, aluminum and vanadium (e.g., 6-4) alloys of titanium, cobalt chromium alloys, as well as surgical grade steel. Preferred polymeric materials include polyetherether ketone (PEEK) and ultra-high molecular weight polyethylene (UHMWPE). Composites of metal and polymeric materials are also preferred in some aspects. Thus, the additive process may be used to fabricate implants comprised of such materials. Metal implants are highly preferred.

Additive processes may comprise successively layering by depositing solid material onto a substrate, then sintering or melting the deposited solid material into a layer of the implant, then depositing more solid material onto the previous layer, then sintering or melting the newly deposited layer to both fuse with the previous layer and establish the next layer, and repeating these steps until the implant is completed. The solid material preferably comprises a bulk material in the form of a wire, powder, particles, granules, fragments, or combinations thereof, which is/are sintered or melted by an energy source. The powder, particles, granules, fragments, or combinations thereof preferably are substantially spherical in shape. It is preferred that the powder, particles, granules, fragments, or combinations thereof do not comprise irregular shapes or edges, or jagged edges. The spheres may comprise different sizes, or may be substantially the same size.

The additive process may comprise sintering and/or melting of the powder, particles, granules, wires, fragments, or combinations thereof. The process preferably achieves substantially complete melting of the powder, particles, granules, fragments, or combinations thereof such that the layer being deposited is comprised of substantially fully molten material, the material preferably being metal. Suitable additive processes include, without limitation, selective laser sintering, including, for example, direct metal laser sintering (DMLS) (DMLS® is a service mark of EOS GmbH), selective laser melting, including, for example, laserCUSING™ (Concept Laser Schutzrechtsverwaltungs GmbH), electron beam melting (EBM), fused deposition modeling (FDM), direct metal deposition, laser Engineered Net Shaping (LENS), and wire-based directed energy deposition. Thus, the energy source may comprise a laser or an electron beam, although any suitable technique for melting the material may be used.

Deposition and/or sintering or melting preferably takes place in an inert environment, for example, with low oxygen and/or in the presence of nitrogen and/or argon. In some aspects, a preceding layer (having just been formed) has not substantially solidified prior to the successive layer being deposited thereon. In some aspects, a preceding layer (having just been formed) has at least partially solidified prior to the successive layer being deposited thereon.

In some preferred aspects, the additive building comprises vertically additively building (e.g., from the anterior to the posterior, from the posterior to the anterior, or from one lateral side to the other lateral side) the orthopedic implant. In some preferred aspects, the additive building comprises horizontally additively building (e.g., from the top to the bottom or the bottom to the top) the orthopedic implant. Illustration of an example of an anterior to posterior vertical build is shown in FIG. 1, illustration of a posterior to anterior vertical build is shown in FIG. 2. Illustration of an example of a bottom to top horizontal build is shown in FIG. 3. Layers may first be deposited onto a build plate or a support material, the latter which may include a plurality of the first deposited layers. According to a preferred additive vertical build manufacturing process, the first deposited layer after a support material, if present, constitutes a non-bone-contacting surface such as the anterior face or posterior face of the implant. Successive layers are deposited, then sintered or melted, through the middle of the implant, and until the opposing face (posterior or anterior face) is completed. Bone-contacting surfaces arise from the edges of the layers laid in a vertical build scheme. Bone-contacting surfaces arise from the layers themselves in a horizontal build scheme.

Additive building allows the implants to include complex external and/or internal geometries and shapes. Accordingly, the orthopedic implants may comprise one or more apertures into and/or through one or more of the top, bottom, sides, or other surfaces. The apertures thus may be surrounded by internal surfaces of the implant, of any desired shape or geometry. The internal surfaces may comprise lattice structures. Internal surfaces may be placed in contact with a bone graft material upon implantation within the body.

The additive process may be used to impart at least macro-scale structural features on surfaces of the implant. Thus, the macro-scale features may be created via the additive manufacturing, and may be part of the initial design.

Following completion of building the implant body through the additive process, the implant body may be subject to stress-relieving processing, including a reheat of the formed implant body. Stress relief may be carried out under vacuum and/or an inert gas. The heating may be followed by a cooling step. In some aspects, the reheat may also be accompanied by pressure. The pressure may be either uniaxial (e.g., applied from one direction) or isostatic (e.g., applied evenly from all directions). Hot isostatic pressing (HIP) is highly preferred.

HIP is conducted by placing the implant body in a sealed container which can be heated and pressure controlled by adding and removing gases. Typically, once the implant body is placed in the sealed container, the container is evacuated to remove any contaminating gasses. The container is then heated while introduce an inert gas (for example, Argon) into the chamber to increase the pressure. The container is then held at the elevated temperature and pressure for a period of time, after which the container is rapidly cooled and depressurized.

Hot isostatic pressing is conducted at a temperature below the melting point of the material from which the implant body is made, but at a sufficiently high temperature. The temperature is typically less than 80% of the melting temperature. HIP may proceed according to standard conditions, such as ASTM Standard Specification F3001.

It is believed that HIP results in changes to the implant body. For example, the combination of temperature and pressure results in the collapse of any inclusions present within the implant body. In some aspects, the density of the implant body may be substantially near or equal to 100% following HIP, meaning that the implant may be substantially free of inclusion bodies (internal pores). Removing inter-layer boundaries and removing inclusions improves the mechanical strength of the implant body and reduces the likelihood of failure once implanted.

In addition, the elevated temperature and pressure from HIP encourages a refinement of the grain structure, grain size, grain composition, grain distribution, or any combination thereof. In some aspects, HIP may increase at least the grain size, particularly when coupled to an electron beam melting additive build. HIP may change the grain structure and changes the intergranular boundaries on the implant surfaces.

The additive process is preferably coupled to a refining process that imparts and/or enhances the micro-scale structures and the nano-structures on external and internal surfaces of the implant. The combination of the additive and refining processes establishes the desired balance of macro-structures, micro-structures, and nano-structures on desired surfaces of the implant for facilitating bone in-growth, bone out-growth, osteoinduction, and osseointegration. The refining process follows completion of the implant production by the additive process.

The refining process may include, for example, a form of a subtractive process that may include erosion, for example, mechanical eroding, chemical eroding, and/or electrochemical eroding of implant surfaces. Mechanical eroding includes, but is not limited to, exposure of select surfaces or the entire implant to photo eroding, energy bombardment, abrasive blasting, plasma eroding, laser eroding, machining, drilling, grinding, peening, abrasive blasting (e.g., sand or grit blasting), or any combinations of such processes. Chemical eroding may include, for example, exposure of select surfaces or the entire implant to a chemical such as an acid or base, with the acid or base eroding the metal surfaces that come in contact with the acid or base. The refining process preferably does not impart pores into the surface of the implant, but preferably imparts micro-scale structures and nano-scale structures into one or more desired surfaces of the implant, including one or more internal surfaces. These desired surfaces (e.g., those receiving the refining process treatments) typically will be those that contact bone or a bone graft material when the implant is implanted in the body.

In some aspects, the subtractive refinement process includes mechanical eroding, but not chemical eroding, of one or more additively produced surfaces of the implant. In some aspects, the subtractive refinement process includes chemical eroding, but not mechanical eroding, of one or more additively produced surfaces of the implant. In preferred aspects, the subtractive refinement process includes two subparts—mechanical eroding and chemical eroding. The chemical eroding preferably follows the mechanical eroding. The subtractive refinement process imparts micro-scale structures and nano-scale structures into refined surfaces.

Prior to eroding of select implant surfaces, other surfaces of the implant that are not intended to have micro-scale structures or nano-scale structures, or which have been smoothed, may be protected by masking such surfaces, thereby leaving exposed the other surfaces to be eroded. The exposed surfaces may then be eroded. Mechanical eroding may include particle blasting, for example, using an organic or inorganic eroding media. The media preferably are dissolvable, for example, in an aqueous or acidic medium. In some alternative aspects, the surfaces may be mechanically eroded by tumble finishing (e.g., tumbling the implant in the presence of such media). The tumbling process may be wet (e.g., with a lubricant) or dry. Mechanical eroding preferably imparts micro-scale structural features in eroded surfaces.

Chemical eroding is a preferred subtractive refinement process. Acid eroding comprises one preferred chemical eroding process. Base eroding comprises another preferred chemical eroding process. It is believed that the acids and bases erode the grain structures and grain boundaries in a way that enhances the bioactivity (e.g., bone growth-promoting properties) of the implant surface. Thus, in some aspects, chemical eroding produces nano-scale structural features into the chemically eroded surfaces of the implant. Chemical erosion also can impart micro-scale structural features into the surfaces. Chemical eroding may be done on the mechanically eroded surfaces, such that the chemical-eroded nano-scale structures may overlap with the mechanical-eroded micro-scale structures.

For chemical eroding, one or more surfaces of the implant may be masked to protect those surfaces from the chemical or acid, and exposed, unmasked surfaces that remain can then be eroded. The chemical eroding preferably follows a mechanical eroding step, although in some aspects, only chemical eroding of the implant surfaces is used (no mechanical eroding step is employed). The chemical eroding process may repeated a number of times as necessitated by the amount and nature of the irregularities required for any particular application, or by the desired pattern and erode depth to be produced. Control of the strength of the acid or base, the temperature at which the eroding process takes place, and the time allotted for the eroding process allow fine control over the resulting surface produced by the process. The number of repetitions of the eroding process can also be used to control the surface features. Chemical eroding is preferably accomplished by immersing the implant into the acid solution or in a base solution, but immersion is not required such that the surfaces to be chemically eroded can be brought in contact with the acid or base according to any suitable process.

After the final eroding process, the mask may be removed and the part may be cleaned. The surface may also be passivated, for example, using an aqueous solution comprising nitric acid. The surface may be cleaned and rinsed with water. The implant may be washed in an aqueous environment under agitation and heat with or without a detergent. Following washing, the implant may be dried, for example with hot air, heating in a dry oven, or both Chemical eroding alone of the titanium implant surface has the potential to greatly enhance osseointegration without adding particulate matter (e.g., hydroxyapatite) or embedding surface contaminants (e.g., grit particles).

The refining processing steps can be adjusted to create a mixture of depths, diameters, feature sizes, and other geometries suitable for a particular implant application. The orientation of the pattern of features can also be adjusted. Such flexibility may be desired, for example, in aspects where the surface structural features should be oriented in opposition to the biologic forces that may be applied against the implant upon implantation, and to the insertion direction.

Mechanical eroding, in addition to imparting micro-scale structural features, may also remove or reduce debris from the implant surfaces. Acid eroding, in addition to imparting nano-scale structural features into implant surfaces, may also remove or reduce debris from the implant surfaces. Debris may include external debris such as dirt or other artifacts of handling. External debris may also include particles or components of the media from the mechanical eroding/blasting step, which particles may have become lodged into the implant surface. Debris may also include intrinsic debris, such as artifacts of the additive build process, for example, powder, particles, granules, etc. that were not completely melted or completely sintered during the additive building.

Figure 11:
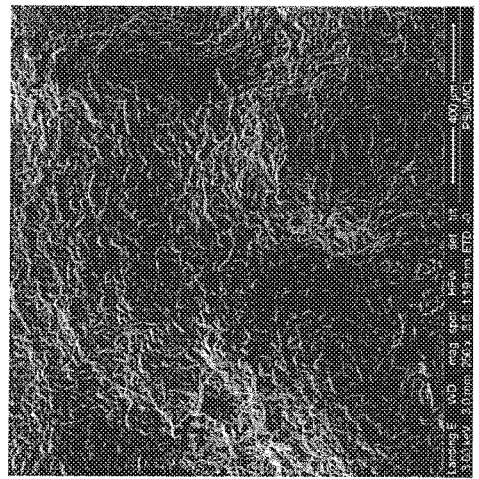
FIG. 11 shows how mechanical erosion and the combination of mechanical and chemical erosion can remove unsintered powder from the additive build. The figure shows SEM images of a surface of a sintered titanium alloy particles at 250× magnification (top row) and at 1500× magnification (bottom row). The left column images show the magnified surface off the machine (as additively built) without any follow-up erosion processing. The center column images show the magnified surface following mechanical erosion after the additive build. The right column images show the magnified surface following sequential mechanical erosion and chemical erosion after the additive build.
Figure 11:
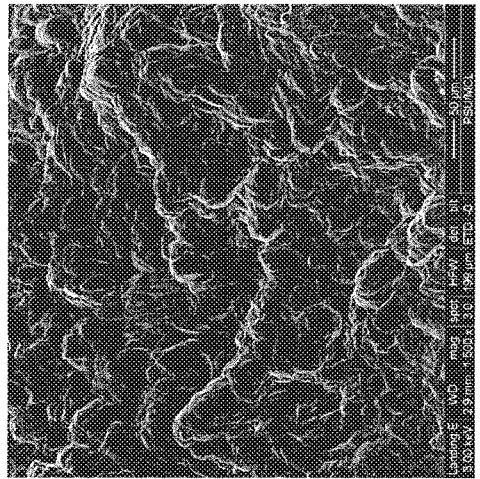
Figure 11:
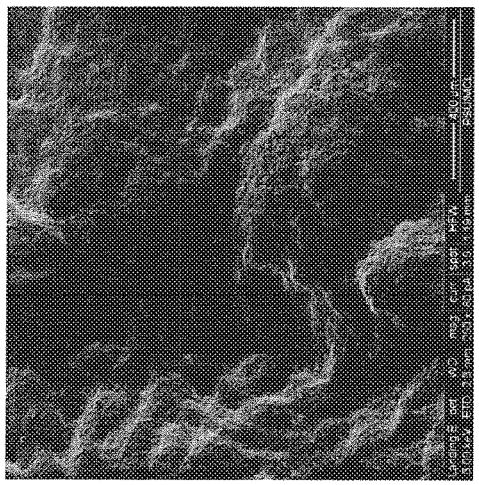
Figure 11:
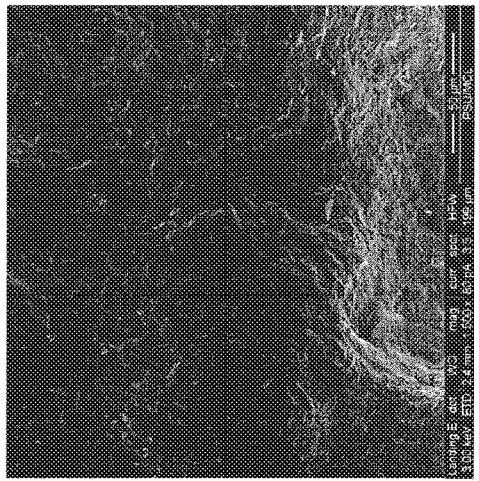
Figure 11:
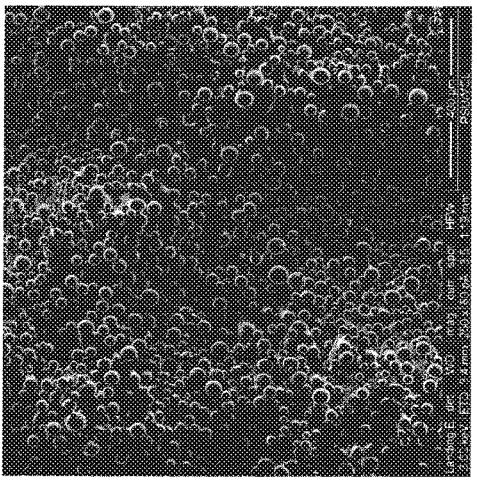
Figure 11:
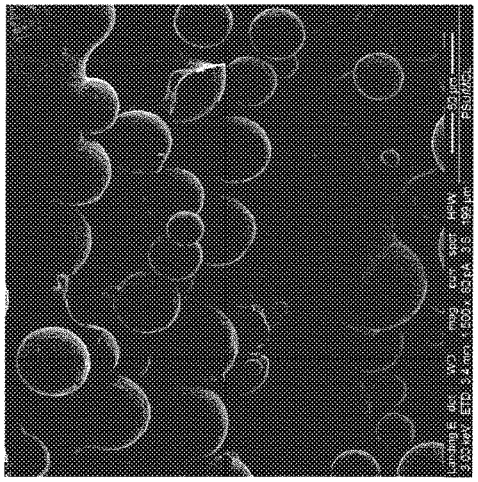

FIG. 11, for example, shows electron micrographs of a titanium surface created from additive building, with the images in the left column (at two different magnifications) illustrating that some particles have not fully integrated from the additive build. Thus, there is a risk that such particles on an implant may dislodge following implantation, and create negative consequences for the patient either locally or systemically. The erosion process thus may be used to remove unsintered/unmelted or incompletely sintered or melted particles from the surfaces, thereby reducing the risk of particle dislodgement.

As shown in the center column of FIG. 11, mechanical erosion can significantly reduce the amount of un-integrated or partially integrated particles from the surface of the additively built structure. And as shown in the right column of FIG. 11, the addition of chemical erosion (following mechanical erosion) can further reduce the amount of un-integrated or partially integrated particles from the surface of the additively built structure.

The subtractive refining process produces micro-scale structural features and nano-scale structural features. These features preferably overlap with macro-scale structural features that are produced from the additive building process.

Macro structural features include relatively large dimensions, for example, dimensions measured in millimeters (mm) or microns (µm). Micro structural features include dimensions that are measured in microns (µm). Nano structural features include dimensions that are measured in nanometers (nm) or microns (µm). Patterns of macro structural features, micro structural features, and/or nano structural features may be organized in regular and/or repeating patterns and optionally may overlap each other, or such features may be in irregular or random patterns, or repeating irregular patterns.

The topography of implant surfaces prepared by additive building, followed by mechanical and/or chemical eroding preferably is roughened, preferably irregular, and comprises macro scale structural features, micro scale structural features, and nano scale structural features, and is also distinct from super-macro scale structural features such as teeth, spikes, grooves, and ridges, and other bone-gripping super-macro scale structures that are typically present on the surface of bone-contacting implants, the latter of which are intended to dig into or score bone. The surface topography produced according to the inventive methods preferably does not damage or score bone, though it may support a friction-type grip of bone surfaces. This surface topography preferably also facilitates and/or enhances osteoinduction and bone growth, and may also facilitate osseointegration of the implant.

The surface topography may be considered bioactive, and induces and/or supports and/or enhances mesenchymal stem cell differentiation and progression, preosteoblast differentiation and progression, and/or osteoblast differentiation and progression. Such differentiation and progression may be characterized by a greater amount or a greater rate of the production growth factors associated with osteoinduction or osteogenesis, for example, following implantation into the body. Differentiation markers include, without limitation, enhanced expression of various forms of bone morphogenic protein and integrin on the cell surface, as well as enhanced expression and/or secretion of growth factors such as osteocalcin (OCN), osterix (OSX), osteoprotegerin, VEGF, and FGF, as well as enhanced expression and/or secretion of alkaline phosphatase (ALP). The mature osteoblast state is characterized by a decrease in ALP, and once the osteoblast differentiates to an osteocyte the expression of both OSX and OCN is decreased as well (Baek W-Y, et al. (2009) J. Bone Miner. Res. 24:1055-65; Zhang C. (2010) J. Orthopaedic Surg. and Res. 5:1; and Tu Q, et al. (2007) Tissue Eng'g. 1:2431-40). In vivo evaluations have revealed that both ALP and OCN are present during fracture healing. In these evaluations both ALP and OCN production is highest in healing bone fractures at 8 weeks post fracture (Leung K S et al. (1993) Bone & Joint Journal. 75:288-92; and Herrmann Metal. (2002) Clin. Chemistry. 48:2263-6). Furthermore, ALP and OCN have been used for in vitro evaluation of the potential for a synthetic material to promote bone formation in vivo. It has been further demonstrated that increased ALP and OCN in vitro associate with synthetic graft success in vivo (Borden M, et al. (2002) J. Biomed. Mater. Res. 61:421-9; Borden M, et al. (2002) Biomaterials. 23:551-9; and Borden M et al. (2004) J. Bone Joint Surg. Br. 86:1200-8). Similar evaluations using titanium mesh have correlated in vitro ALP and osteopontin (a matrix protein secreted earlier in differentiation than OCN) with in vivo success (Datta N (2005) Biomaterials. 26:971-7; Bancroft G N (2002) Proc. Natl. Acad. Sci. U.S.A. 99:12600-5; and Sikavitsas V I et al. (2003) J. Biomed. Mater. 67A:944-51).

It is believed that the surfaces ultimately facilitate osseointegration (e.g., formation of a direct structural and functional interface between the artificial implant and living bone or soft tissue) with the surrounding living bone. The surfaces produced according to the invention are believed to support new bone growth in the absence of direct contact with bone or a bone graft material, though the surfaces also support new bone growth when placed in direct contact with bone or a bone graft material. It is believed that new bone growth may initiate on the surfaces of implants produced according to the invention, as distinct from growth of bone from surrounding tissue of the body into the implant surfaces. Thus, implant fixation may depend, at least in part, on the stimulation and proliferation of bone modeling and forming cells, such as osteoclasts and osteoblasts and like-functioning cells upon the implant surface. It is believed that these cells attach more readily to microscopically rough surfaces (e.g., those having micro-scale and nano-scale structural features) rather than smooth surfaces, including surfaces with macro-scale structural features that are too large to be recognized by cells. In this manner, a surface may be bioactive due to its ability to stimulate cellular attachment and bone growth.

The refined surfaces are composed of various sizes of features that, at the microscopic level, interact with the tissues and stimulate their natural remodeling and growth. At a larger scale (e.g., macro-scale structural features), implant surface structures perform the function of generating non-stressful friction with tissue in the body (e.g., with adjacent bone) that, when combined with a surgical technique that retains the most rigid cortical bone structures in the disc space, allow for a friction fit that does not abrade, chip, perforate, or compromise the bone surface.

As the macro features are primarily formed via the additive manufacture process, additional refinement steps may be sequentially applied, in turn, to form the micro-scale and nano-scale structural features of the implant surfaces (e.g., external and internal surfaces). Mechanical eroding is believed to primarily form or enhance the micro-scale structural features. Chemical eroding is believed to primarily form or enhance the nano-scale structural features, but can also form or enhance the micro-scale structural features. Macro-scale structure-forming mechanical and/or acid eroding may be used in addition to the additive manufacture process that produces macro-scale features or, in some aspects, may be used instead of additive manufacturing. For example, the additive manufacturing may produce substantially featureless surfaces, with mechanical and/or chemical eroding then applied to such surfaces to produce all three of the macro-scale, micro-scale, and nano-scale structures on the surfaces.

Each of the macro-scale structures, the micro-scale structures, and the nano-scale structures, both individually and in combination and in sub-combination establish a roughness on the implant surface. The roughness may be measured according to one or more of the roughness parameters established by the International Organization for Standardization (ISO), e.g., ISO 468:1982. Several separate parameters can be used to characterize the surface roughness. Such parameters include, but are not limited to, Rp (max height profile), Rv (max profile valley depth), Rz (max height of the profile), Rc (mean height of the profile), Rt (total height of the profile), Ra (arithmetic mean deviation of the profile), Rq (root mean square deviation of the profile), Rsk (skewness of the profile), Rku (kurtosis of the profile), RSm (mean width of the profile), RΔq (Root mean square slope of the profile), Rmr (material ratio of the profile), Rδc (profile section height difference), lp (sampling length–primary profile), lw (sampling length–waviness profile), lr (sampling length–roughness profile), ln (evaluation length), Z(x) (ordinate value), dZ/dX (local slope), Zp (profile peak height), Zv (profile valley depth), Zt (profile element height), Xs (profile element width), and Ml (material length of profile). Other parameters may include Rsa (surface area increase), Rpc (peak counts), H (Swedish height), ISO flatness (areal flatness deviation), Pt ISO (peak-to-valley profile height), Rtm (mean peak-to-valley roughness), Rv (lowest value), Rvm (mean valley profile depth), Ry (maximum peak-to-valley roughness), Rpm (mean peak areal height), S (average spacing between local peaks), SM (average spacing between peaks at the mean line), summit number, summit density, summit spacing, valley number, valley density, and valley spacing.

Average Amplitude Ra. Ra comprises an arithmetic average height. Mathematically, Ra may be computed as the average distance between each roughness profile point and the mean line.

In mathematical terms, this process can be represented by the following Formula I:

$$Ra = \frac{1}{n}\sum_{i=1}^{n}|y_i|$$

Average Peak-to-Valley Roughness Rz. The average peak-to-valley roughness, Rz, is defined by the ISO and ASME 1995 and later. Rz is based on one peak and one valley per sampling length. The RzDIN value is based on the determination of the peak-to-valley distance in each sampling length. These individual peak-to-valley distances are averaged, resulting in the RzDIN value.

Maximum Peak-to-Valley Height Rmax. The maximum peak-to-valley height, Rmax, comprises the maximum peak-to-valley distance in a single sampling.

Figure 10:
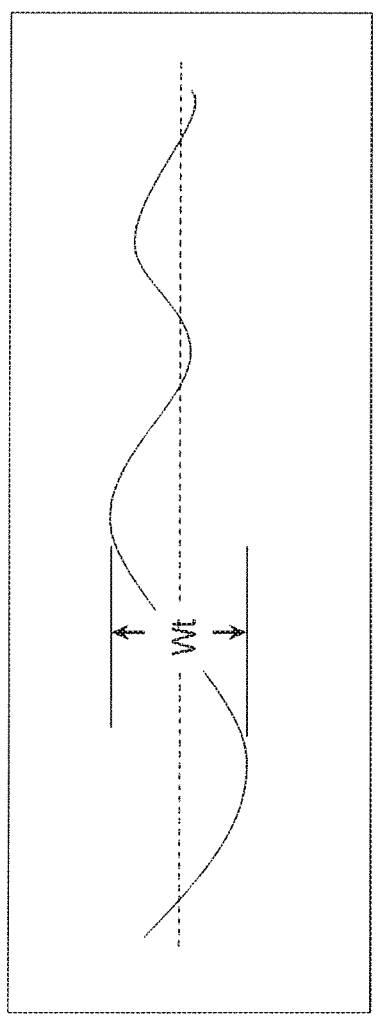
FIG. 10 graphically represents the total peak-to-valley of waviness of profile macro-, micro-, or nano-scale surface features and structure.

Total Peak-to-Valley of Waviness Profile Wt. The total peak-to-valley of waviness profile (over the entire assessment length) is illustrated in FIG. 10.

Mean Spacing Sm. The mean spacing, Sm, comprises the average spacing between positive mean line crossings. The distance between each positive (upward) mean line crossing is determined and the average value is calculated.

In some aspects, the micro-scale structural features comprise a micro peak-to-valley height, Rmax, of from about 1 to about 200 micrometers. In some aspects, the micro peak-to-valley height is less than 100 micrometers and greater than 1 micrometer, less than about 95 micrometers and greater than 1 micrometer, less than about 90 micrometers and greater than 1 micrometer, or less than about 80 micrometers and greater than 1 micrometer. In some aspects, the micro peak-to-valley height is from about 5 to about 25 micrometers, from about 6 to about 16 micrometers, from about 10 to about 125 micrometers, from about 10 to about 100 micrometers, from about 10 to about 90 micrometers, from about 10 to about 150 micrometers. In some aspects, the micro mean peak-to valley height is from about 1 to about 150 micrometers, from about 1 to about 100 micrometers, from about 1 to about 125 micrometers, from about 1 to about 95 micrometers, from about 1 to about 90 micrometers, from about 1 to about 80 micrometers, from about 1 to about 70 micrometers, from about 1 to about 50 micrometers, from about 1 to about 25 micrometers, from about 2 to about 100 micrometers, from about 2 to about 90 micrometers, from about 2 to about 80 micrometers, from about 2 to about 25 micrometers, from about 3 to about 40 micrometers, from about 3 to about 30 micrometers, from about 4 to about 120 micrometers, from about 4 to about 40 micrometers, from about 4 to about 30 micrometers, from about 5 to about 40 micrometers, from about 5 to about 30 micrometers, from about 7 to about 20 micrometers, from about 7 to about 15 micrometers, from about 8 to about 14 micrometers, or from about 9 to about 13 micrometers.

The micro-scale structural features may comprise a skewness of from about −2 to about 2, from about −2 to about 1.5, from about −2 to about 1, from about 2 to about −1, from about −2 to about 0, or from about 0 to about 2. In some aspects, the micro-scale skewness is from about −1.5 to about 1.5, from about −1.5 to about 1, from about −1.5 to about 0, from about −1 to about 1.5, from about −1 to about 1, from about −1 to about 0, from about from about −0.5 to about 2, from about −0.5 to about 1.5, from about −0.5 to about 1, from about −0.5 to about 0.5, from about −0.5 to about 0.4, from about −0.4 to about 0, from about 0 to about 0.4, from about −0.3 to about 0.3, from about −0.3 to about 0, from about 0 to about 0.3, from about −0.25 to about 0.25, from about −0.25 to about 0, from about 0 to about 0.25, from about −0.2 to about 0.2, from about −0.2 to about 0, from about 0 to about 0.2, from about −0.15 to about 0.15, from about −0.15 to about 0, from about 0 to about 0.15, from about −0.1 to about 0.1, from about −0.1 to about 0, from about 0 to about 0.1, from about −0.05 to about 0.05, from about −0.05 to about 0, or from about 0 to about 0.05.

The micro-scale structural features may comprise a kurtosis of from about 1 to about 9. The micro-scale kurtosis may be from about 1 to about 8.5, from about 1 to about 8, from about 1 to about 7.5, from about 1 to about 7, from about 1 to about 6.5, from about 1 to about 6, from about 1 to about 5.5, from about 1 to about 5, from about 1 to about 4.5, from about 1 to about 4, from about 1 to about 3.5, from about 1 to about 3, from about 1 to about 2.5, from about 1 to about 2, from about 2 to about 5, from about 2 to about 4.5, from about 2 to about 4, from about 2 to about 3.5, from about 3 to about 5, from about 3 to about 4.5, from about 3 to about 4, from about 2.5 to about 4.5, from about 2.5 to about 4.4, from about 2.5 to about 4.2, from about 2.5 to about 4, from about 2 to about 4.4, from about 2 to about 4.3, from about 2 to about 4.2, from about 2 to about 4.1, from about 2 to about 3.9, from about 2 to about 3.8, from about 2 to about 3.7, from about 2 to about 3.4, from about 2 to about 3.3, from about 2 to about 3.2, from about 2.4 to about 3.4, from about 2.4 to about 3.1, from about 2.4 to about 2.9, from about 3.1 to about 4, from about 3.1 to about 3.9, from about 3.1 to about 3.8, or from about 3.1 to about 3.7.

In some aspects, the nano peak-to-valley height, Rmax, is from about 0.001 to about 20 micrometers. In some aspects, the nano peak-to-valley height, Rmax, is from about 0.001 to about 10 micrometers. In some aspects, the nano peak-to-valley height, Rmax, is from about 0.001 to about 50 micrometers, from about 0.001 to about 20 micrometers, from about 0.001 to about 10 micrometers, from about 0.001 to about 5 micrometers, from about 0.001 to about 3 micrometers, from about 0.001 to about 2 micrometers, or from about 0.001 to about 1 micrometers. In some aspects, the nano peak-to-valley height is from about 0.5 to about 1.5 micrometers, or from about 0.8 to about 1.4 micrometers. In some aspects, the nano peak-to valley height is from about 0.01 to about 20 micrometers, from about 0.01 to about 10 micrometers, from about 0.01 to about 5 micrometers, from about 0.05 to about 25 micrometers, from about 0.05 to about 10 micrometers, from about 0.05 to about 5 micrometers, from about 0.1 to about 10 micrometers, from about 0.1 to about 5 micrometers, from about 0.1 to about 1.5 micrometers, from about 0.001 to about 0.5 micrometers, from about 0.005 to about 5 micrometers, from about 0.005 to about 20 micrometers, from about 0.005 to about 2.5 micrometers, from about 0.006 to about 1.6 micrometers, from about 0.007 to about 1.5 micrometers, from about 0.009 to about 1.3 micrometers, from about 0.02 to about 10 micrometers, from about 1 to about 15 micrometers, from about 5 to about 15 micrometers, from about 10 to about 20 micrometers, or from about 1 to about 20 micrometers. In some aspects, the nano peak-to-valley height, Rmax, is from about 0.001 to about 0.6 micrometers, from about 0.001 to about 0.5 micrometers, from about 0.001 to about 0.4 micrometers, from about 0.001 to about 0.3 micrometers, from about 0.001 to about 0.2 micrometers, from about 0.001 to about 0.1 micrometers, from about 0.001 to about 0.09 micrometers, from about 0.001 to about 0.08 micrometers, from about 0.001 to about 0.07 micrometers, from about 0.001 to about 0.06 micrometers, from about 0.001 to about 0.05 micrometers, from about 0.001 to about 0.04 micrometers, from about 0.001 to about 0.03 micrometers, or from about 0.001 to about 0.02 micrometers.

The following examples are provided to describe the invention in greater detail. The examples are intended to illustrate, not to limit, the invention.

Example 1

Implant Surfaces Additive and Subtractive Manufacture Process

A number of test discs of a titanium alloy including 6% aluminum and 4% vanadium were fabricated using either laser sintering or electron beam melting (EBM) by either layering from the bottom surface to the top surface (horizontal) or by layering from the anterior surface to the posterior surface (vertical). For each layer, the titanium alloy particles were deposited, first onto a platform surface of the additive manufacturing device, and then successively onto melt-assembly of each layer. The particles were melted together by laser sintering or EBM. Accordingly, the top surface of a test disc fabricated in a horizontal build direction is parallel to the deposited layers, and the top surface of a test disc fabricated in a vertical build direction is perpendicular to the deposited layers.

Following additive fabrication, the unrefined test discs were divided into two groups. The first group was further subject to heat treatment and the second group was not. The test discs were heat treated according to ASTM F3001.

Some of the test discs were then subject to surface refinement by blasting and eroding. The blasted surfaces were immersed in an acid solution. After acid eroding, the discs were immersed in water to quench the eroding reaction.

The refined surface was then inspected by scanning electron beam microscopy, scans of which are included as FIGS. 4-9.

Figure 4:
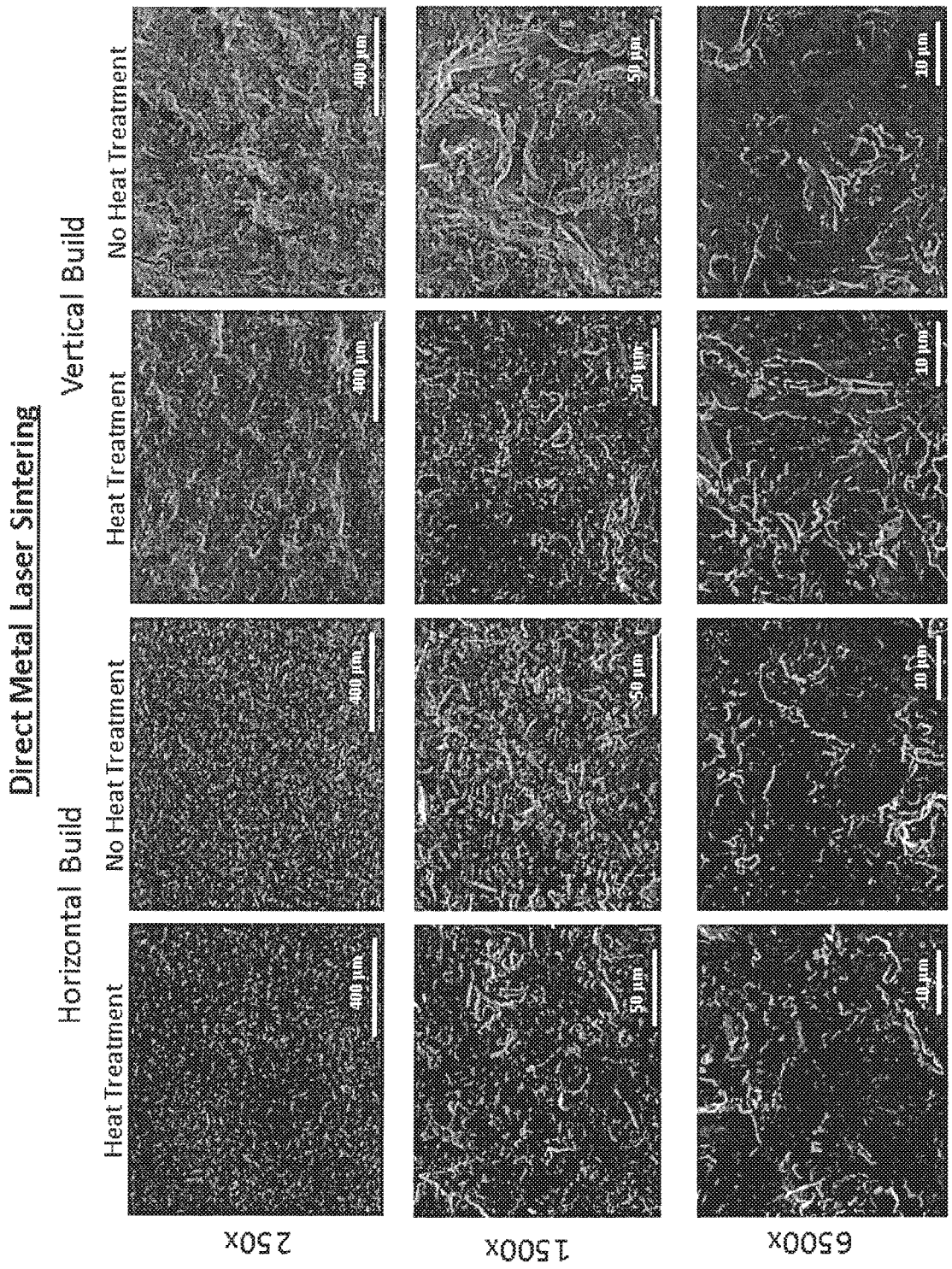
FIG. 4 shows electron micrographs of test disc surfaces, in which the discs were prepared by laser sintering are compared: Left-most column, laser sintering-assembled disc prepared by layering from the bottom to the top (horizontal build), followed by heat treatment; Left-center column, laser-sintering-assembled disc prepared by layering from the bottom to the top (horizontal build), without subsequent stress-relieving heat treatment; Right-center column, laser-sintering-assembled disc prepared by layering from the anterior to the posterior (vertical build), followed by stress-relieving heat treatment; Right-most column, laser-sintering-assembled disc prepared by layering from the anterior to the posterior (vertical build), without subsequent stress-relieving heat treatment.
Figure 5:
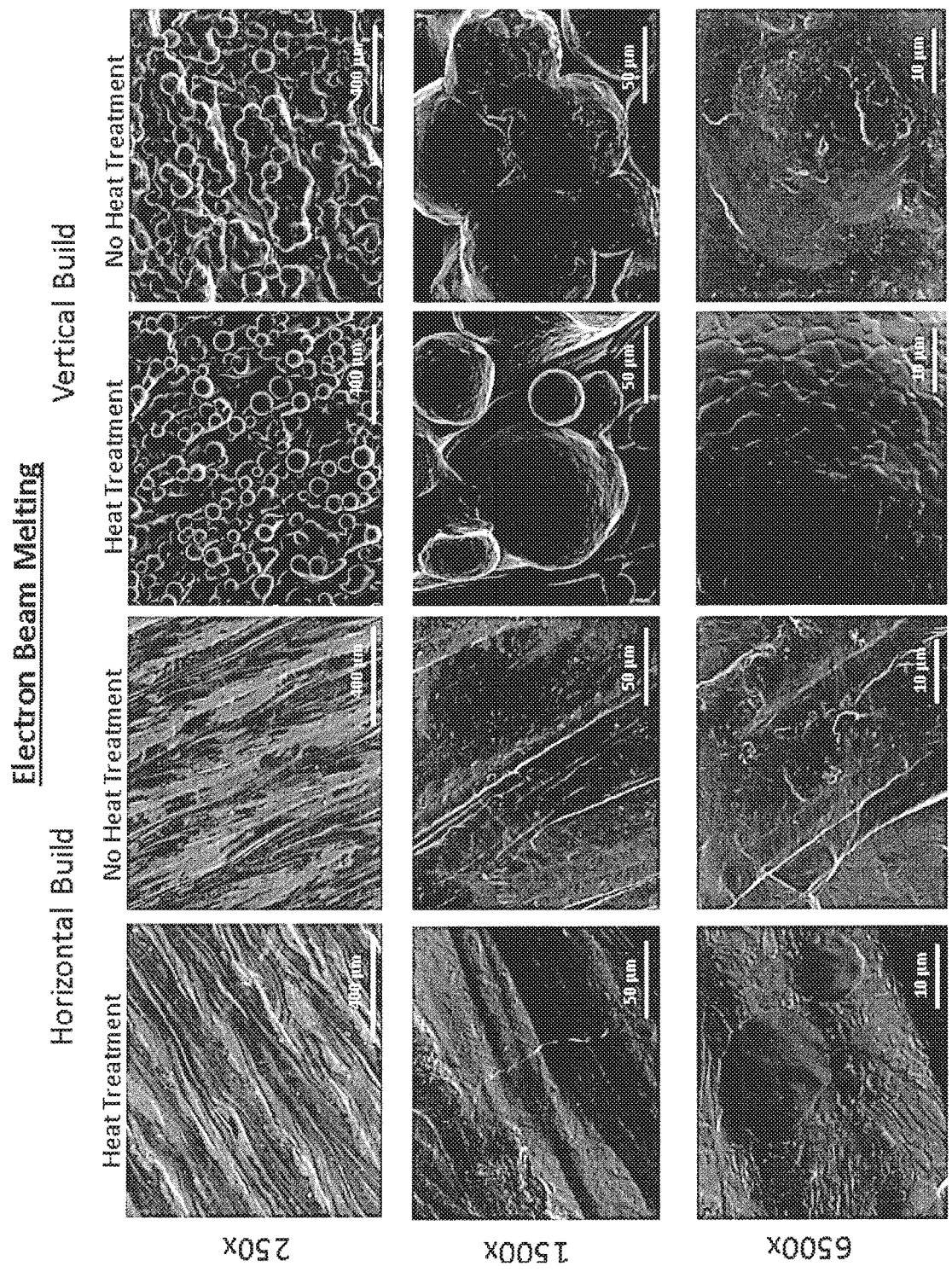
FIG. 5 shows electron micrographs of test disc surfaces, in which the discs were prepared by Electron beam melting (EBM) are compared: Left-most column, EBM-assembled disc prepared by layering from the bottom to the top (horizontal build), followed by hot isostatic pressing (HIP); Left-center column, EBM-assembled disc prepared by layering from the bottom to the top (horizontal build), without subsequent HIP; Right-center column, EBM-assembled disc prepared by layering from the anterior to the posterior (vertical build), followed by HIP; Right-most column, EBM-assembled disc prepared by layering from the anterior to the posterior (vertical build), without subsequent HIP.

FIGS. 4-5 includes electron micrographs of test discs prior to surface refinement. FIG. 4 compares discs produced by laser sintering in both horizontal and vertical build directions, as well as the effect of heat treatment prior to surface refinement. FIG. 5 compares discs produced by EBM in both horizontal and vertical build directions, as well as the effect of heat treatment prior to surface refinement. Each of FIGS. 4 and 5 includes a grid of twelve electron micrographs. In each figure, the top row includes micrographs taken with 250× magnification, the middle row includes micrographs taken with 1500× magnification, and the bottom row includes micrographs taken with 6500× magnification. Each row includes, from left to right, (1) a horizontally built disc subject to heat treatment, (2) a horizontally built disc not subject to heat treatment, (3) a vertically built disc subject to heat treatment, and (4) a vertically built disc not subject to heat treatment.

As can be seen from each of FIGS. 4 and 5, for each combination of additive process (e.g., laser sintering or EBM), build direction (vertical or horizontal), and heat treatment (HIP for EBM test discs, vacuum heating for laser sintering test discs, or no heat treatment), some micro scale structures (features generally sized from 1 µm to 100 µm) and essentially no nano scale structures (features generally sized from 1 to 100 nm) are present on the surface of the test discs. Although the test discs produced by EBM are rough on a macro (include macro scale features generally sized greater than 100 µm) and micro scale, the test discs produced by laser sintering are smooth even at a macro and micro scale, each in the absence of secondary processing. It is believed that the micro scale of the EBM discs is a result of the layers and partially sintered powder.

Figure 6:
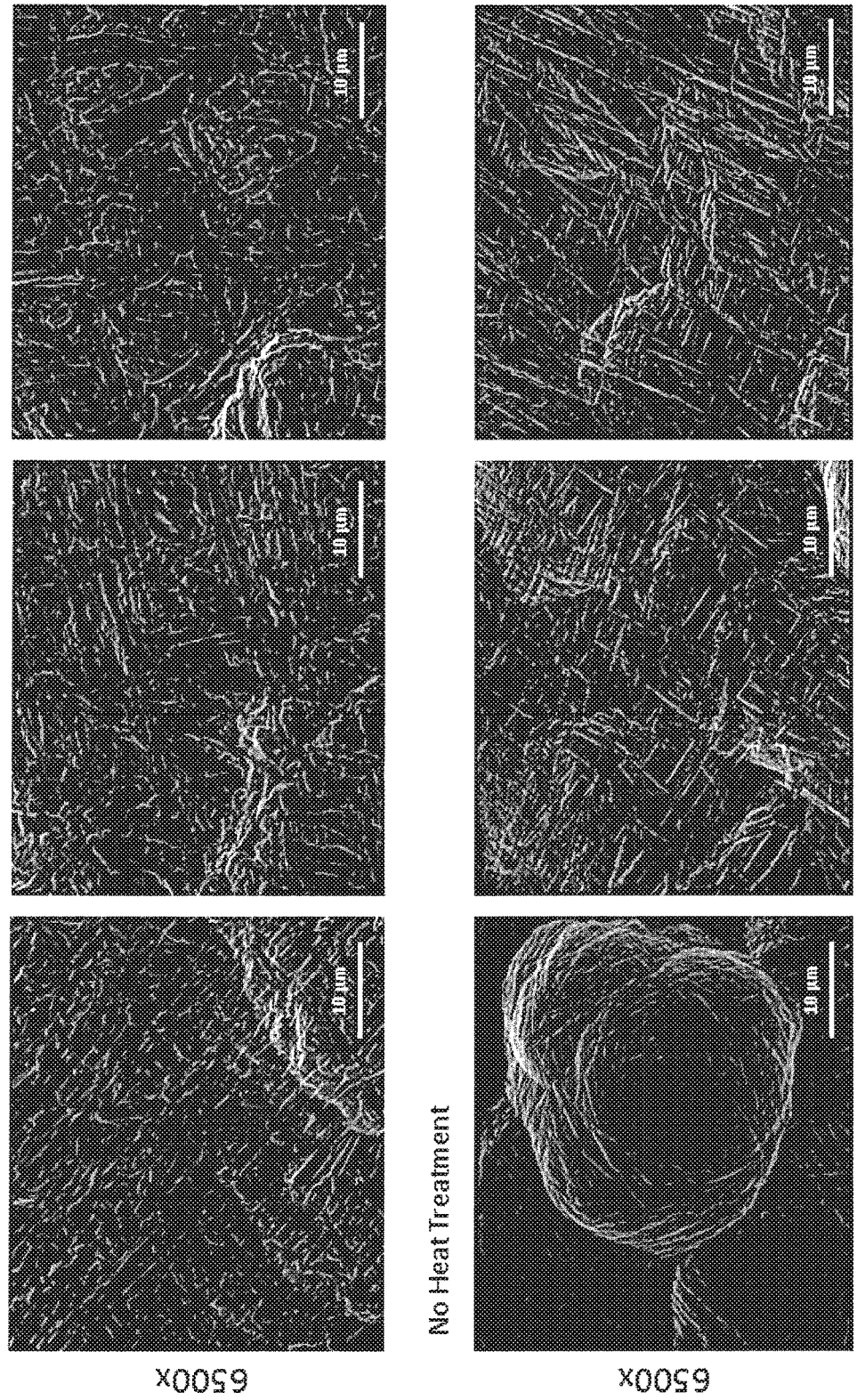
FIG. 6 shows electron micrographs of test disc surfaces, in which the discs were prepared by laser sintering, layering from the bottom to the top (horizontal build), followed by surface eroding, are compared. Top row, laser sintering-assembled disc, horizontal build, followed by heat treatment, followed by surface eroding; Bottom row, laser sintering-assembled disc, horizontal build, without heat treatment, followed by surface eroding.
Figure 7:
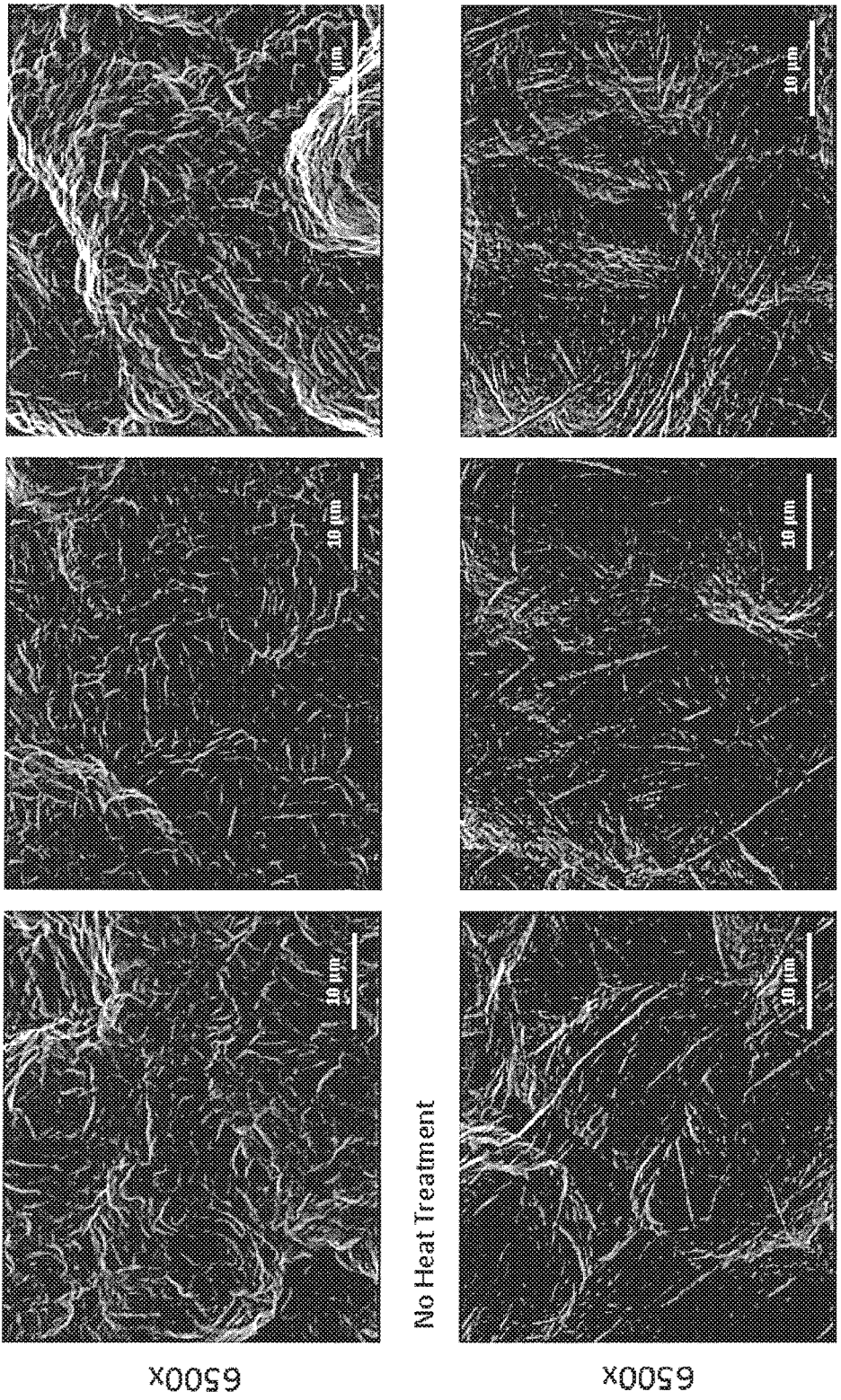
FIG. 7 shows electron micrographs of test disc surfaces, in which the discs were prepared by laser sintering, layering from the anterior to the posterior (vertical build), followed by surface eroding, are compared. Top row, laser sintering-assembled disc, vertical build, followed by heat treatment, followed by surface eroding; Bottom row, laser sintering-assembled disc, vertical build, without heat treatment, followed by surface eroding.
Figure 8:
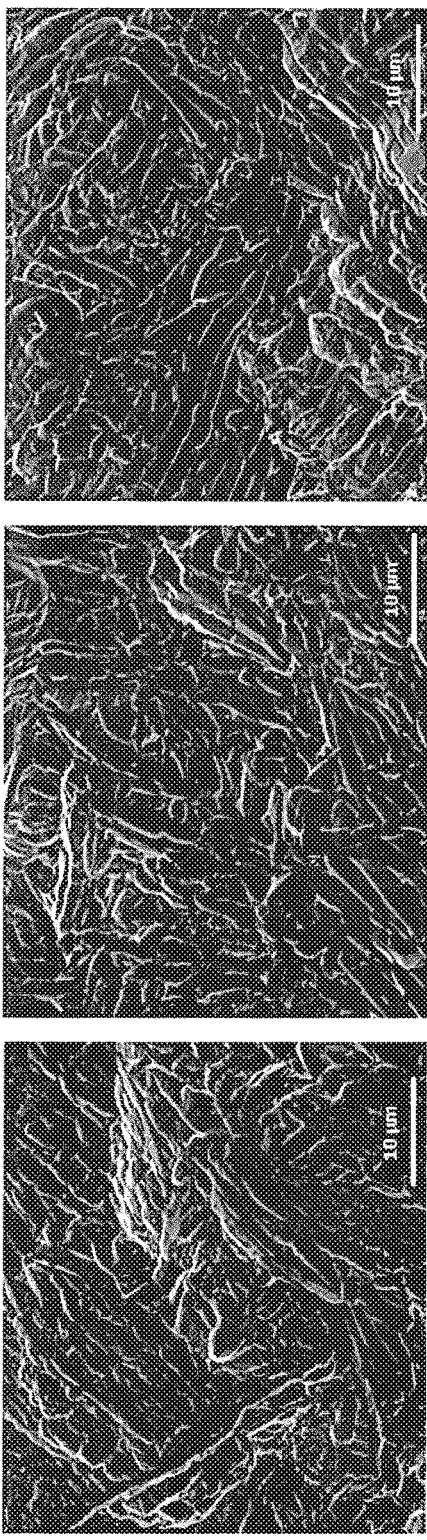
FIG. 8 shows electron micrographs of test disc surfaces, in which the discs were prepared by EBM, layering from the bottom to the top (horizontal build), followed by surface eroding, are compared. Top row, EBM-assembled disc, horizontal build, followed by HIP, followed by surface eroding; Bottom row, EBM-assembled disc, horizontal build, without HIP, followed by surface eroding.
Figure 8:
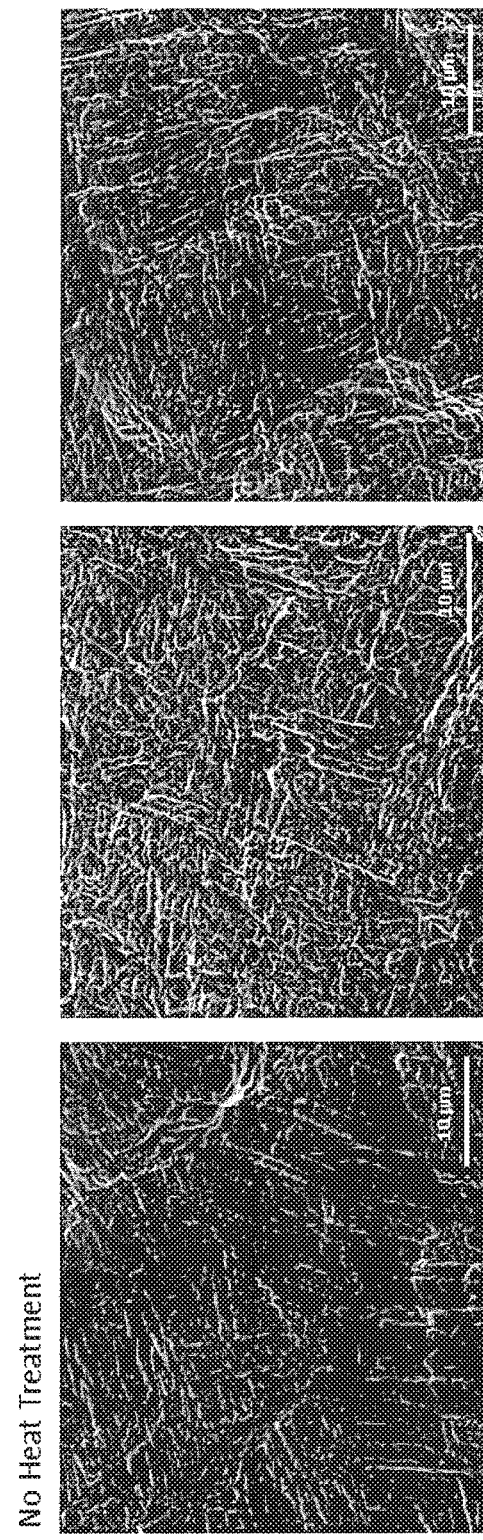
Figure 9:
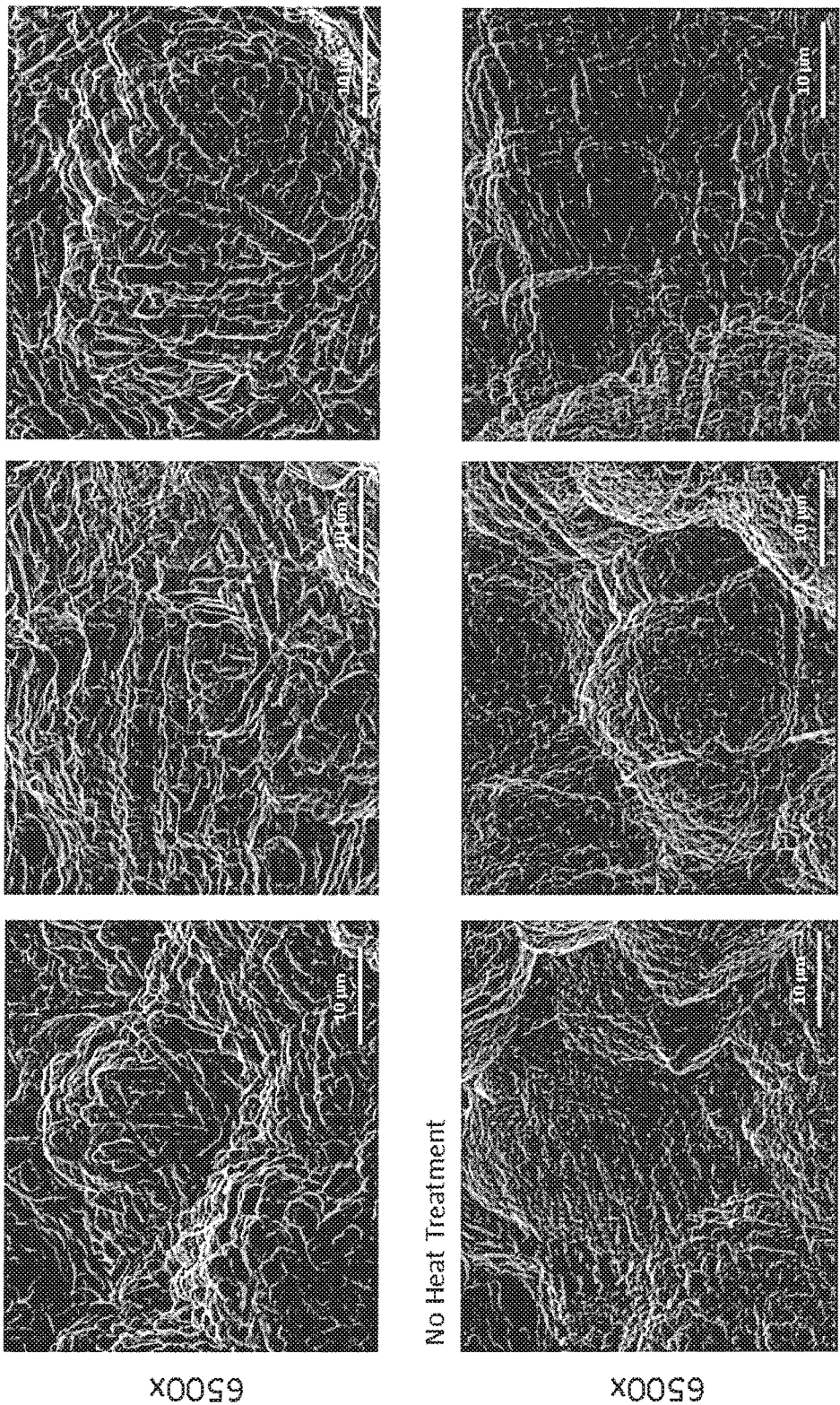
FIG. 9 shows electron micrographs of test disc surfaces, in which the discs were prepared by EBM, layering from the anterior to the posterior (vertical build), followed by surface eroding, are compared. Top row, EBM-assembled disc, vertical build, followed by HIP, followed by surface eroding; Bottom row, EBM-assembled disc, vertical build, without HIP, followed by surface eroding.

FIGS. 6-9 include electron micrographs of test discs following surface refinement. FIG. 6 compares the effect of heat treatment on discs produced by laser sintering in a horizontal build direction. FIG. 7 compares the effect of heat treatment on discs produced by laser sintering in a vertical build direction. FIG. 8 compares the effect of heat treatment on discs produced by EBM in a horizontal build direction. FIG. 9 compares the effect of heat treatment on discs produced by EBM in a vertical build direction. Each of FIGS. 6-9 includes a grid of six electron micrographs. Each micrograph is taken with a magnification of 6500×. The top row of each of FIGS. 6-9 includes electron micrographs of test discs which were subject to heat treatment. The bottom row of each of FIGS. 6-9 includes electron micrographs of test discs which were not subject to heat treatment.

Referring to FIG. 6, it can be seen that eroding the surface of the laser sintering test disc with a horizontal build direction subject to heat treatment resulted in low density micro-scale and nano-scale structures. Eroding the surface of the laser sintering test disc with a horizontal build direction not subject to heat treatment resulted in a low density of additional micro-scale structures and no additional nano-scale structures.

Referring to FIG. 7, it can be seen that eroding the surface of the laser sintering test disc with a vertical build direction subject to heat treatment resulted in a high density of micro-scale structures and nano-scales structures. Eroding the surface of the laser sintering test disc with a vertical build direction not subject to heat treatment resulted in a moderate density of micro-scale features, but only a low density of nano scale structures.

Referring to FIG. 8, it can be seen that eroding the surface of the EBM test disc with a horizontal build direction subject to heat treatment resulted in a moderate density of micro-scale structures but only a low density of nano-scale structures. Eroding the surface of the EBM test disc with a horizontal build direction not subject to heat treatment also resulted in a moderate density of micro-scale structures but only a low density of nano-scale structures. However, the resulting surface features differed based on whether the test disc was heat treated. A preferential eroding of the grain boundaries is observed, with wider elongated features on the heat treated versus non heat treated parts.

Referring to FIG. 9, it can be seen that eroding the surface of the EBM test disc with a vertical build direction subject to heat treatment resulted in a high density of both micro-scale and nano-scale structures. However, eroding the surface of the EBM test disc with a vertical build direction not subject to heat treatment resulted in only a moderate density of micro-scale structures and a low density of nano-scale structures.

As can be seen from Table 1, for both laser sintering and EBM, the presence of micro scale features and nano-scale features is dependent on both the build direction and heat treatment. For a given build direction and heat treatment, laser sintering and EBM produce approximately equal densities of micro-scale and nano-scale structures.

TABLE 1

Density of Micro Scale and Nano Scale Features

| Build Method | Build Direction | Heat Treatment | Micro Scale Structures | Nano Scale Structures |
|---|---|---|---|---|
| laser sintering | Horizontal | Yes | ++ | + |
| laser sintering | Horizontal | No | + | − |
| laser sintering | Vertical | Yes | +++ | +++ |
| laser sintering | Vertical | No | ++ | + |
| EBM | Horizontal | Yes | ++ | + |
| EBM | Horizontal | No | ++ | + |
| EBM | Vertical | Yes | +++ | +++ |
| EBM | Vertical | No | ++ | + |

− = no or minimal additional structures,
+ = low density of additional structures,
++ = moderate density of additional structures, but less than the desired amount,
+++ = high density of additional structures For a given additive process and a given build direction, the density of micro-scale and nano-scale structures is increased by heat treating the test disc after additive fabrication but before surface refinement. Without being bound to any particular theory, it is believed that the heat treatment enhances the surface of the test disc and makes the surface of the test disc more receptive to the surface refining by changing the grain structures on the surface of the test disc.

Further, for a given additive process and heat treatment, the density of micro-scale and nano-scale structures is increased by building the test disc in a vertical rather than horizontal orientation. Without being bound to any particular theory, it is believed that building the test disc in a vertical direction aligns the metal grains in a direction which results in a greater number of grain boundaries being present on the top surface of the test disc. Accordingly, the eroding processes are able to affect a greater area of the surface and produce a greater density of micro-scale and nano-scale structures.

The invention is not limited to the embodiments described and exemplified above, but is capable of variation and modification within the scope of the appended claims.

What is claimed is:

1. A process for producing a metal orthopedic implant, the process comprising:
vertically additively building a metal orthopedic implant comprising an alloy of titanium, aluminum and vanadium and having macro-scale structures, wherein the metal orthopedic implant comprises an anterior side, a posterior side, a top side, a bottom side, and an aperture formed through one or more of the anterior side, the posterior side, the top side or the bottom side,
the posterior side and the anterior side are external non-bone contacting surfaces, the bottom side and the top side are external bone contacting surfaces and the aperture is surrounded by at least one internal surface of the metal orthopedic implant, and vertically additively building comprises producing layers from the anterior side to the posterior side or from the posterior side to the anterior side such that the top side and the bottom side result from one or more edges of the layers and metal grains are aligned in a direction resulting in a greater number of grain boundaries present on the top side or the bottom side, and,
in any order, stress-relieving the metal orthopedic implant or heating the metal orthopedic implant and compressing the heated metal orthopedic implant with hot isostatic pressure or hot uniaxial pressure,
mechanically eroding one or more external bone contacting surfaces and the at least one internal surface surrounding the aperture of the metal orthopedic implant to impart micro-scale structures into the one or more external bone contacting surfaces and the at least one internal surface of the metal orthopedic implant, and
chemically eroding one or more external bone contacting surfaces and the at least one internal surface of the metal orthopedic implant to impart nano-scale structures into the one or more external bone contacting surfaces and the at least one internal surface of the metal orthopedic implant.

2. The process according to claim 1, wherein the micro-scale structures comprise a maximum peak-to-valley height of from 1 μm to 200 μm.

3. The process according to claim 1, wherein the micro-scale structures comprise a skewness of from −2 to 2.

4. The process according to claim 1, wherein the nano-scale structures comprise a maximum peak to valley height of from 0.001 μm to 20 μm.

5. The process according to claim 1, wherein the alloy of titanium, aluminum and vanadium comprises 6 percent aluminum and 4 percent vanadium.

6. A process for producing a metal orthopedic implant, the process comprising:
additively building a metal orthopedic implant comprising an alloy of titanium, aluminum and vanadium and having macro-scale structures, wherein the metal orthopedic implant comprises an anterior side, a posterior side, a top side, a bottom side, and an aperture formed through one or more of the anterior side, the posterior side, the top side or the bottom side,
the posterior side and the anterior side are external non-bone contacting surfaces, the bottom side and the top side are external bone contacting surfaces and the aperture is surrounded by at least one internal surface of the metal orthopedic implant, and additively building comprises producing layers from the anterior side to the posterior side or from the posterior side to the anterior side such that the top side and the bottom side result from one or more edges of the layers and metal grains are aligned in a direction resulting in a greater number of grain boundaries present on the top side or the bottom side, and,
in any order, stress-relieving the metal orthopedic implant or heating the metal orthopedic implant and compressing the heated metal orthopedic implant with hot isostatic pressure or hot uniaxial pressure, and
mechanically eroding one or more external bone contacting surfaces and the at least one internal surface surrounding the aperture of the metal orthopedic implant to impart micro-scale structures into the one or more external bone contacting surfaces and the at least one internal surface of the metal orthopedic implant, and
chemically eroding one or more external bone contacting surfaces or the at least one internal surface of the metal orthopedic implant to impart nano-scale structures into the one or more external bone contacting surfaces or the at least one internal surface of the metal orthopedic implant.

7. The process according to claim 6, wherein additively building the implant comprises vertically building the implant.

8. The process according to claim 6, wherein additively building the implant comprises melting or sintering powder, particles, granules, wires, fragments, or combinations thereof of the metal into the shape of the implant.

9. The process according to claim 6, wherein heat treating the implant comprises heating the implant and compressing the heated implant with hot uniaxial pressure.

10. The process according to claim 6, wherein compressing the heated implant comprises hot isostatic pressure to substantially eliminate internal pores of the metal.

11. The process according to claim 10, wherein the hot isostatic pressure is carried out at a temperature less than 80 percent of a melting temperature of a material from which the implant body is made.

12. The process according to claim 6, wherein the micro-scale structures comprise a maximum peak-to-valley height of from 1 μm to 200 μm.

13. The process according to claim 12, wherein the nano-scale structures comprise a maximum peak-to-valley height of from 0.001 μm to 5 μm.

14. The process according to claim 12, wherein the micro-scale structures comprise a skewness of from −2 to 2.

15. The process according to claim 12, wherein the micro-scale structures comprise a kurtosis of from 1 to 9.

16. The process according to claim 6, wherein the nano-scale structures comprise a maximum peak to valley height of from 0.001 μm to 20 μm.

\* \* \* \* \*